US010518057B2

(12) United States Patent
Harrison et al.

(10) Patent No.: US 10,518,057 B2
(45) Date of Patent: Dec. 31, 2019

(54) FACIAL INTERFACE AND HEADGEAR SYSTEM FOR USE WITH VENTILATION AND POSITIVE AIR PRESSURE SYSTEMS

(71) Applicants: Donald Harrison, Park City, UT (US); Andrew Havens Gosline, Cambridge, MA (US); Veaceslav Gheorghe Arabagi, Cambridge, MA (US); Aaron Jonah Kapelus, Jamaica Plain, MA (US)

(72) Inventors: Donald Harrison, Park City, UT (US); Andrew Havens Gosline, Cambridge, MA (US); Veaceslav Gheorghe Arabagi, Cambridge, MA (US); Aaron Jonah Kapelus, Jamaica Plain, MA (US)

(73) Assignee: HUMAN DESIGN MEDICAL, LLC, North Billerica, MA (US)

( * ) Notice: Subject to any disclaimer, the term of this patent is extended or adjusted under 35 U.S.C. 154(b) by 1194 days.

(21) Appl. No.: 14/801,091

(22) Filed: Jul. 16, 2015

(65) Prior Publication Data
US 2016/0015924 A1 Jan. 21, 2016

Related U.S. Application Data

(60) Provisional application No. 62/025,073, filed on Jul. 16, 2014, provisional application No. 62/025,077, filed on Jul. 16, 2014, provisional application No. 62/049,994, filed on Sep. 12, 2014.

(51) Int. Cl.
*A61M 16/06* (2006.01)
*A61M 16/10* (2006.01)
*A61M 16/00* (2006.01)
*A61M 16/08* (2006.01)
*A61M 16/22* (2006.01)

(52) U.S. Cl.
CPC .... *A61M 16/0683* (2013.01); *A61M 16/0066* (2013.01); *A61M 16/0605* (2014.02); *A61M 16/0622* (2014.02); *A61M 16/0666* (2013.01); *A61M 16/0816* (2013.01); *A61M 16/0875* (2013.01); *A61M 16/1045* (2013.01); *A61M 16/22* (2013.01); *A61M 2016/0661* (2013.01); *A61M 2205/0216* (2013.01)

(58) Field of Classification Search
CPC .......... A61M 16/0666; A61M 16/0616; A61M 16/0683; A61M 16/0672; A61M 16/0677; A61M 16/06; A62B 25/005; A62B 18/084; A62B 18/02; A62B 18/025; B64D 2231/025; B64D 45/00; Y10S 128/26
See application file for complete search history.

(56) References Cited

U.S. PATENT DOCUMENTS 3,599,636 A * 8/1971 Gutman ............... A62B 18/084
128/207.11
4,367,735 A * 1/1983 Dali .................. A61M 16/0683
128/203.22

(Continued)

*Primary Examiner* — Bradley H Philips
*Assistant Examiner* — Victoria Murphy
(74) *Attorney, Agent, or Firm* — Yi Liu

(57) ABSTRACT

The present disclosure relates to a mask assembly system that has an adjustable headgear system with an inflatable cushion connected to the positive air pressure supply for conforming to a user's face.

14 Claims, 22 Drawing Sheets

(56) References Cited

U.S. PATENT DOCUMENTS

| | | | |
|---|---|---|---|
| 4,422,456 A * | 12/1983 | Tiep | A61M 16/0666 128/207.17 |
| 4,437,462 A * | 3/1984 | Piljay | A62B 18/084 128/207.11 |
| 4,915,105 A * | 4/1990 | Lee | A62B 18/00 128/205.27 |
| 5,269,296 A * | 12/1993 | Landis | A61M 16/0666 128/204.18 |
| 5,477,852 A * | 12/1995 | Landis | A61M 16/0666 128/204.18 |
| 5,538,000 A * | 7/1996 | Rudolph | A61M 16/06 128/201.22 |
| 5,664,566 A * | 9/1997 | McDonald | A62B 18/02 128/205.25 |
| 5,954,052 A * | 9/1999 | McDonald | B64D 10/00 128/206.27 |
| 6,039,045 A * | 3/2000 | Bertheau | A62B 18/084 128/206.27 |
| 6,431,172 B1 * | 8/2002 | Bordewick | A61M 16/0666 128/206.11 |
| 6,470,887 B1 * | 10/2002 | Martinez | A62B 18/084 128/207.11 |
| 6,533,983 B2 * | 3/2003 | Curti | A61M 16/0666 128/204.18 |
| 6,561,193 B1 * | 5/2003 | Noble | A61M 16/01 128/207.18 |
| 6,588,424 B2 * | 7/2003 | Bardel | A62B 17/04 128/206.21 |
| 6,684,883 B1 * | 2/2004 | Burns | A61M 16/0666 128/206.11 |
| 7,004,170 B1 * | 2/2006 | Gillstrom | A61M 16/0666 128/206.11 |
| 7,178,525 B2 * | 2/2007 | Matula, Jr. | A61M 16/0666 128/206.27 |
| 7,178,526 B2 * | 2/2007 | McDonald | A62B 18/02 128/207.11 |
| 7,318,437 B2 * | 1/2008 | Gunaratnam | A61M 16/0666 128/206.11 |
| 7,337,780 B2 * | 3/2008 | Curti | B29C 33/485 128/207.18 |
| 7,658,189 B2 * | 2/2010 | Davidson | A61M 16/06 128/205.25 |
| 8,025,058 B2 * | 9/2011 | Chandran | A61M 16/0666 128/207.11 |
| 8,151,796 B2 * | 4/2012 | McDonald | A62B 18/084 128/201.24 |
| 8,291,906 B2 * | 10/2012 | Kooij | A61M 16/0666 128/206.24 |
| 8,297,285 B2 * | 10/2012 | Henry | A61M 16/06 128/207.18 |
| 9,027,557 B2 * | 5/2015 | Dussart | A62B 18/084 128/206.11 |
| 9,717,872 B2 * | 8/2017 | Chodkowski | A61M 16/0683 |
| 9,895,505 B2 * | 2/2018 | Guney | A61M 16/06 |
| 2007/0246043 A1 * | 10/2007 | Kwok | A61M 16/0666 128/201.22 |
| 2008/0060649 A1 * | 3/2008 | Veliss | A61M 16/06 128/205.25 |
| 2008/0083412 A1 * | 4/2008 | Henry | A61M 16/0683 128/207.11 |
| 2010/0018534 A1 * | 1/2010 | Veliss | A61M 16/06 128/206.24 |
| 2010/0024811 A1 * | 2/2010 | Henry | A61H 9/0078 128/202.16 |
| 2014/0261440 A1 * | 9/2014 | Chodkowski | A61M 16/0683 128/206.24 |
| 2015/0174354 A1 * | 6/2015 | Matula, Jr. | A61M 16/06 128/202.27 |
| 2016/0030696 A1 * | 2/2016 | Klenner | A61M 16/0066 128/207.18 |
| 2016/0158475 A1 * | 6/2016 | Harrison | A61M 16/0616 128/201.13 |

* cited by examiner

FACIAL INTERFACE AND HEADGEAR SYSTEM FOR USE WITH VENTILATION AND POSITIVE AIR PRESSURE SYSTEMS

PRIORITY CLAIM

Priority is claimed to U.S. Provisional Patent Application Ser. No. 62/025,073, filed Jul. 16, 2014, 62/025,077, filed Jul. 16, 2014, and 62/049,994 filed Sep. 12, 2014 which are hereby incorporated herein by reference in their entirety.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to medical devices, and, more particularly to mask and headgear portions of air delivery devices that assist with the delivery of gas to the nasal passages of users. These mask and headgear systems and devices may be used with positive airway pressure [PAP] such as continuous positive airway pressure devices [CPAP], automatic positive airway pressure devices [APAP], variable positive airway pressure devices [VPAP], and bi-level positive airway pressure devices [BPAP].

2. Description of the Prior Art

Nasal pillows exist to be partially inserted into a user's nare and form a seal with the nare(s), which allows for the user to breathe from the ventilator or PAP device. However, nasal pillows have been known to not necessarily form the best seals for all users, put unnecessary pressure on the nare region when held in place by a mask system, and limited on flexibility. Masks have also tended to be bulky and shift when wearing them at night. Designs are being made to make masks lighter and more secure.

A need therefore exists for a nasal pillow that is interchangeable with a mask system, which is flexible and adaptable to a user's nare and facial profile, and reduces pressure applied on the nare region while in use. A need also exists for an adjustable mask and headgear system that conforms to a user's head and facial features while being comfortable and securely attaching the nasal pillows to a user's nares.

SUMMARY OF THE INVENTION

Contemplated herein is a facial interface and headgear system for use with ventilation and positive air pressure systems. The facial interface can include a system and assembly configured to provide a portion of continuous airway pressure to a user's airways.

In one embodiment a mask and headgear assembly is comprised of a mask frame, where the mask frame further comprises: a core having an inlet connector for receiving a supply of pressurized gas from a delivery tube; a right arm extending from the core; and a left arm extending from the core, wherein each of the right and left arms form an associated air pathway through each respective arm, wherein each arm includes an first aperture for supplying the supply of pressurized gas to a patient's airways; and a headgear interface located about a distal end of each arm, the headgear interface being configured to be attached to a headgear assembly, the headgear interface further comprising a second aperture for communicating a portion of the supply of pressurized gas to an interior portion of the headgear assembly.

The mask and headgear assembly can further include an inflatable cushion configured to inflate in response to the supply of pressurized gas delivered through the second aperture.

The inflatable cushion can include a deformable core configured to be selectively deformed and retain a deformed shape.

The inflatable cushion can include a plurality of $CO_2$ washout vents provided on an exterior wall. The plurality of $CO_2$ washout vents can be formed from knife-coating a silicone layer over a flexible material, where the material was previously gas permeable and the silicone layer formed thereon or partially embedded therein helps trap in oxygen, but enables CO2 to escape through the silicone knife coated material.

The system can further include a nasal pillow assembly configured to connect to each of the arms over the respective apertures. In this manner each nasal pillow assembly can be configured to communicate the supply of pressurized gas from the air pathway through each nasal pillow assembly and to a user's nostrils.

Optionally, a headgear interface can be provided which is located about a distal end of each of the right and left arms, the headgear interface being configured to be attached to a headgear assembly.

In some embodiments the right and left arms can be offset with respect to one another so as to be non-coaxial, or in other words angled with respect to one another. In yet other embodiments the nasal pillow assembly includes a nasal pillow rotatable about a nasal pillow axis.

In some embodiments the headgear interface provided at each distal end of the left and right arms can include a deformable sidepiece configured to attach to its respective arm. This deformable sidepiece can be configured to attach to the arm at various angular positions with respect to the axis of its respective right or left arm. In some embodiments the deformable sidepiece as a planar member which is configured to be selectively deformed out of plane so as to conform about the facial contours of a user, for example, to hold a shape corresponding to the curvature of the user's cheeks. It will be appreciated that this deformable sidepiece represents a potentially uncomfortable situation wherein the deformable sidepiece could be pressed into the user's face. As such, a malleable cover, such as fabric or neoprene can be provided and configured to encompass the deformable sidepiece.

In some embodiments the nasal pillow assembly can further include an attachment sleeve configured to engage with each of the right and left arms respectively and encompass the associated aperture. The attachment sleeve can thus be configured to provide rotation of each pillow assembly about its respective arm without obstructing flow through the respective aperture. In some embodiments the attachment sleeve includes a radial hose connection for interfacing with its respective nasal pillow. This radial hose connection can be configured to allow for axial adjustable along the radial hose.

In yet other embodiments the attachment sleeve can be provided with one or more washout vents. Alternatively, washout vents can be provided at distal ends of the right and left arms, or about the core, or in any combination of the same.

In some embodiments the nasal pillows can formed in the shape of a cone, the cone having an elliptical cross section. In this manner as the pillows are rotated about a central pillow axis, or about the axis of the radial hose the relative orientation of each pillow can be adjusted so as to match the nostrils or nares of the user.

In some embodiments the headgear can include a plurality of adjustable straps so as to be adjustable to provide a desired retention force or a desired sealing force as well as be customizable so as to match the specific contours of the user's head. In some embodiments one strap can be configured to extend over a crown of the user's head, and in other embodiments a strap can be configured to extend behind a rear portion of the user's head, or both.

The deformable sidepiece of the mask and headgear assembly can attach to each arm using an interference interconnector comprising a male connection and a female connection located selectively about either the deformable sidepiece or the interference interconnector.

In some embodiments the inlet connector can include a swivel connector so as to provide a certain degree of flexibility with respect to an air supply hose and the mask frame provided about the user's face, for example if the user shifts while sleeping.

In some embodiments alternative core or mask frames can be devoid of an attachment sleeve or have arms that pivot about the core.

In some embodiments the core can be provided with a heat moisture exchange (HME) component 326 located within the central portion. Alternatively, the HME 326 can be provided within the air supply hose, or within the right or left arms In yet additional embodiments a method of providing a pressurized stream of air using the device described above is contemplated. The method can include various steps, in varying combinations including: providing a supply of pressurized gas to a delivery tube; receiving the supply of pressurized gas at an inlet of a core; selecting a pair of properly sized nasal pillows from a plurality of various nasal pillows, each nasal pillow having a pillow aperture formed at a top end; affixing the pair of nasal pillows to the core over the respective apertures of each arm such that the air pathway extends through the pillow aperture of each pillow; and positioning the nasal pillows such that the air pathway extends to a user's respiratory system through the nasal pillows through the user's nares.

The method can also include the steps of: affixing a headgear assembly to distal ends of both the right and left arms; and rotating the nasal pillows such that the elliptical cross section coincides with the user's particular nare shape, wherein each of the nasal pillows has an elliptical axial cross section.

These and other embodiments form some of the various inventive concepts as contained herein. The individual embodiments as described are not intended to be limiting, but are intended only as illustrative of the various inventive concepts and are not intended to be limiting except as claimed below.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

Reference will now be made to the exemplary embodiments illustrated, and specific language will be used herein to describe the same. It will nevertheless be understood that no limitation of the scope of the invention is thereby intended though the exemplary embodiments discussed, but the examples are for purposes of illustration of the inventive concepts.

DETAILED DESCRIPTION OF THE PREFERRED EMBODIMENT

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below may be combined with one another in any suitable manner and may be adapted and applied to other PAP apparatuses, systems, and methods, including, but not limited to, APAP, VPAP, and BPAP apparatuses, ventilators, systems, and methods.

The present application seeks to provide a solution to the aforementioned problems by creating an adjustable, comfortable, mask assembly system that has interchangeable components, light-weight, and adaptable to individual users.

Figure 2:
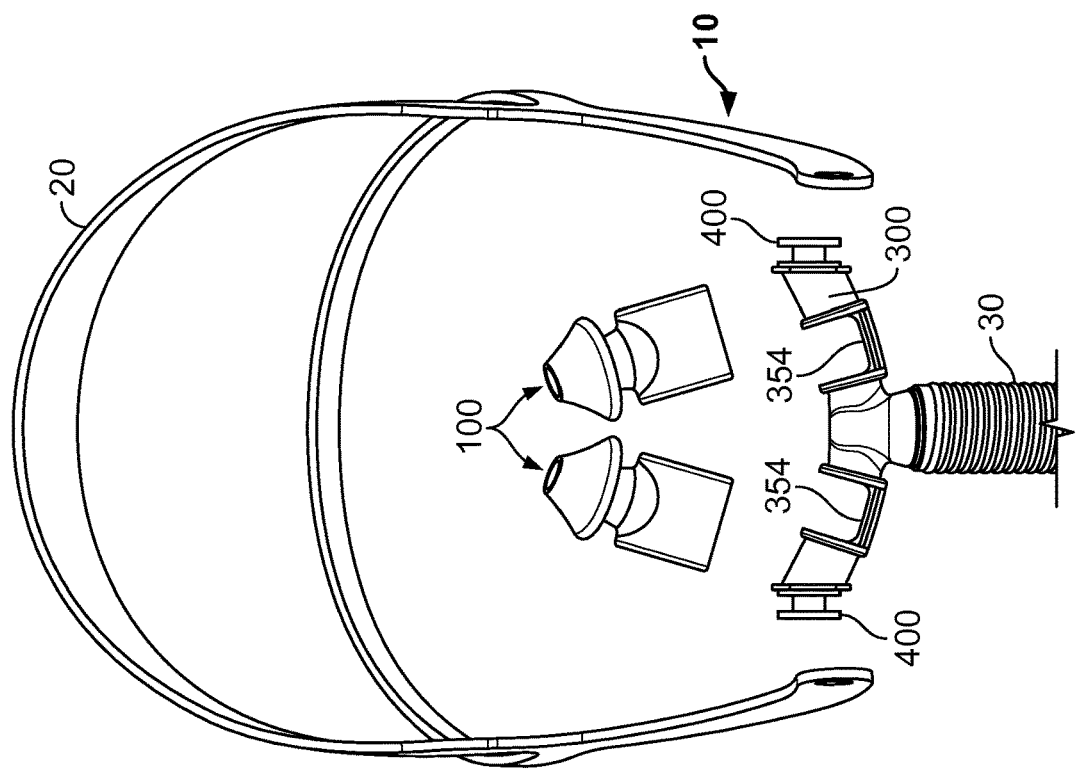
FIG. 2 illustrates a front exploded view of the facial interface and headgear system for use with ventilation and positive air pressure systems of FIG. 1.
Figure 1:
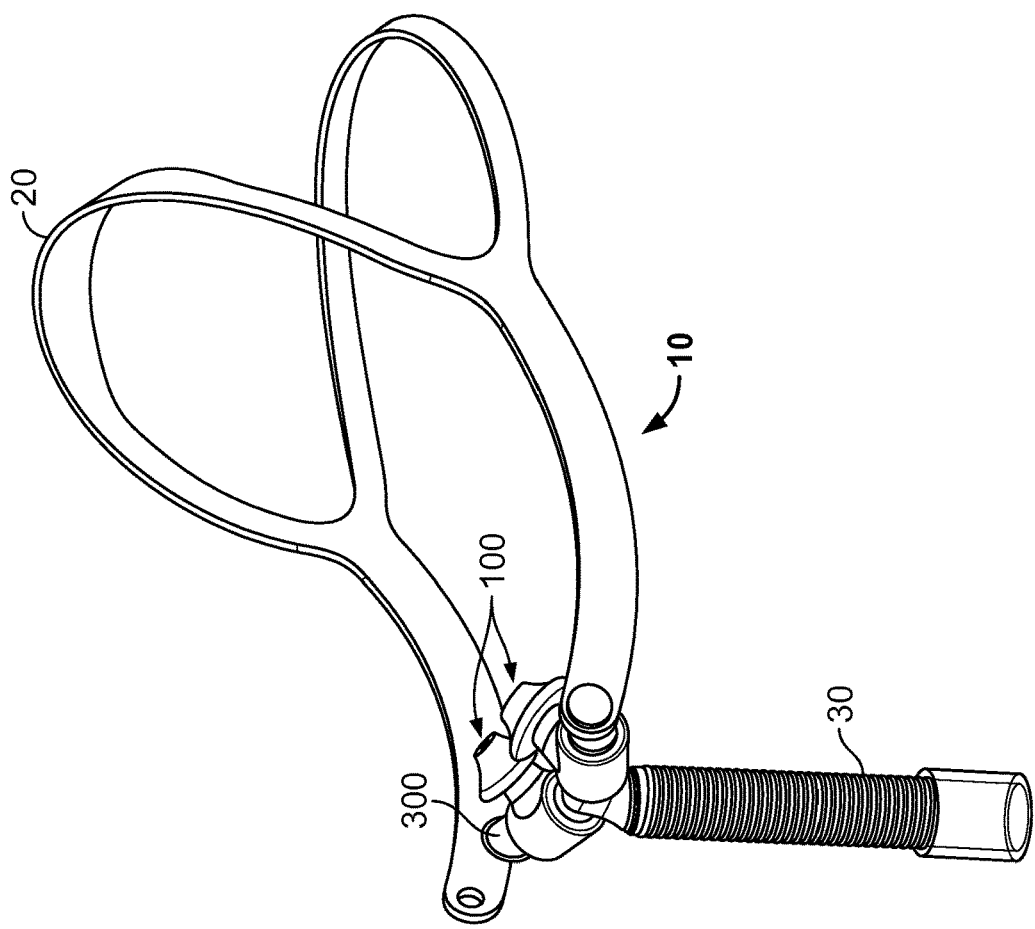
FIG. 1 illustrates a perspective view of a facial interface and headgear system for use with ventilation and positive air pressure systems.
Figure 7:
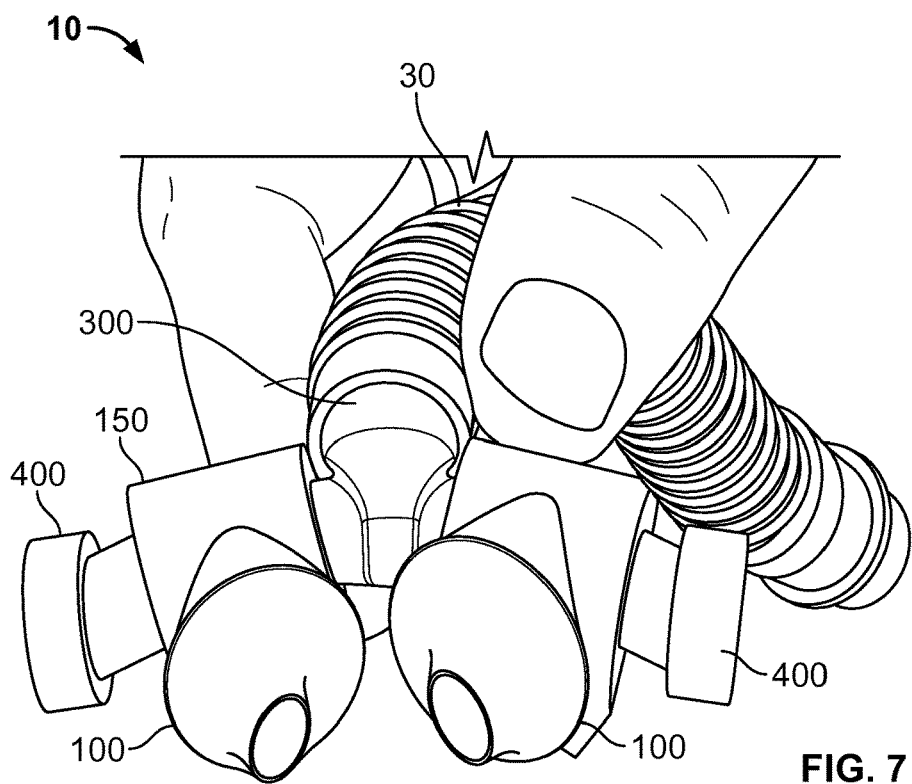
FIG. 7 illustrates a top view of the ventilation and positive air pressure systems of FIGS. 1-2.

FIGS. 1-2, and 7 illustrate various views of a positive airway pressure assembly 10 configured to aid in supplying a stream of positive pressure air to the airways of a patient wearing the assembly 10. The assembly includes a mask frame 300 having a pair of nasal pillow assemblies 100 attached thereto. The mask frame 300 receives a stream of pressurized air from a blower (not shown), which can be attached to the mask frame 300 by means of a supply hose 30. The air then travels through the mask frame 300 through apertures 354 and through the associated pillow assemblies 100 to provide air into the nostrils or nares of the user wearing the positive airway pressure assembly 10.

The positive airway pressure assembly 10 can optionally include a headgear system 20 configured to provide a sealing force between the individual pillow assemblies 100 and the nostrils of the user. In certain cases the headgear system 20 can also provide a positioning force between the mask frame 300 and the maxilla of the user or patient, for example on the portion of the face between the upper lip and below the nose. It will be appreciated that the headgear assembly 20 can be formed of a resilient material, or be adjustable through various means so as to conform to the individual user's contours which, understandably, vary between various users. Further, the headgear assembly 20 can also be configured to affix to distal ends of the mask frame 300 and can be configured to provide a certain degree of rotational adjustment between the mask frame 300 and the headgear 20.

As shown in various figures, headgear 20 may be comprised of multiple straps, such as one configured to go over the top portion of a user's head, and second strap going generally about the back portion of a user's head. Either strap can have an adjustment mechanism, no adjustment mechanism, formed of resilient material, inflexible or formed in a variety of configurations including having a cover or sleeve formed over a portion of the straps or no cover or sleeve.

Figure 3:
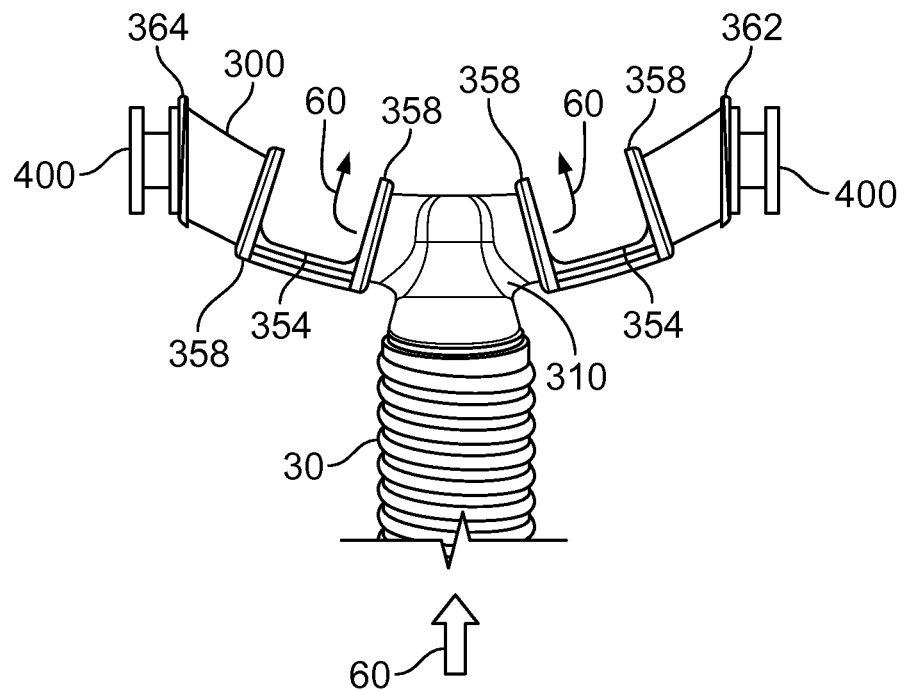
FIG. 3 illustrates a core or mask frame structure for use with the facial interface and headgear system for use with ventilation and positive air pressure systems of FIGS. 1-2.
Figure 4:
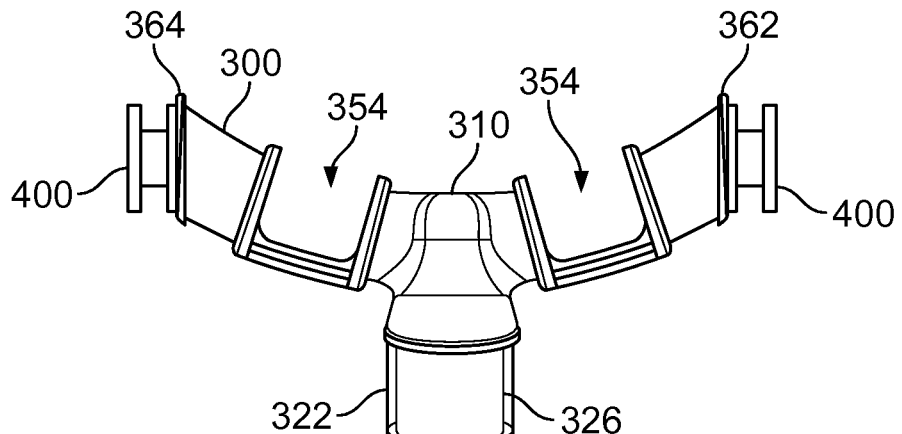
FIG. 4 illustrates an exploded view of the core or mask frame structure of FIG. 3 illustrating a swivel adapter and heat moisture
Figure 4:
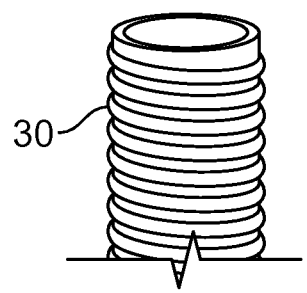
Figure 5:
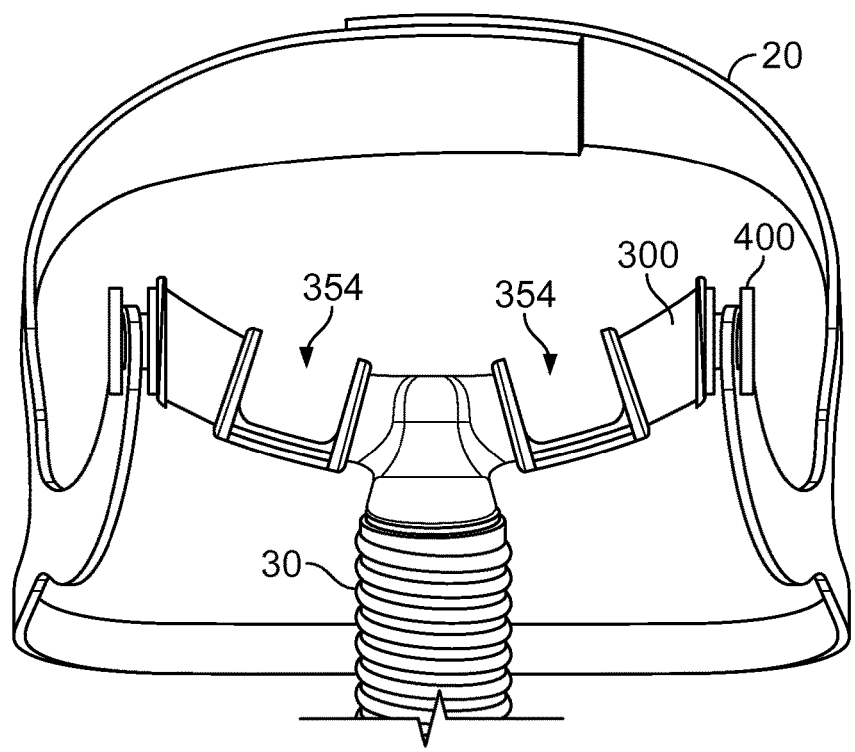
FIG. 5 illustrates an exemplary headgear system attached to the core or mask frame structure of FIG. 3.

FIGS. 3-5 illustrate various aspects of the mask frame 300. It will be appreciated that air supply travels as shown by pathway arrows 60 through the tube, through a central portion of the mask frame 300 and exits apertures 354. The apertures can have a pair of lips or shoulders 358 upon or about which the pillow assembly 100 from FIGS. 1-2 can rest and seal. The mask frame 300 can have a central portion 310 and left and right arms extending therefrom, 362 and 364 respectively. Each of the right and left arms can be provided with a headgear connection interface 400 about their respective distal ends. The headgear connection interface allows for variation in the types of connectors used for connecting the headgear (not shown here).

In some embodiments, the right and left arms can be provided as co-axial, i.e. straight with respect to each other, so as to reduce fabrication complexity and cost. Alternatively, and as shown herein the right and left arms can be angled with respect to one another so as to better conform in shape to the front of the user's face, which understandably typically has a curved profile.

In addition the mask frame or core 300 can be provided with an inlet connector 322 about the central portion. The inlet connector can be configured to swivel coaxially with the air supply hose 30. In addition the core or mask frame 300 can be provided with a heat moisture exchange (HME) component within the core about the inlet connector 322. The HME can also be provided in alternative locations as well as in multiples, for example a pair of HME units could be provided within the nasal pillow assemblies or more proximal the apertures 354.

In particular, FIG. 5 illustrates how the headgear can be affixed to the core or mask frame 300 through the use of one embodiment of a headgear connection interface 400. This particular embodiment illustrates a swivel connection 322 which allows the headgear to rotate with respect to the distal ends of the mask frame 300.

FIGS. 6A-E illustrate various views of a nasal pillow assembly 100 for use with the nasal mask frame as shown in FIGS. 3-5. The nasal pillow assembly 100 can include a nasal pillow 110 and attachment sleeves 150. The attachment sleeves 150 in this embodiment are configured to slide over the mask frame 300 and seal over apertures 354 by having an inner shoulder 359 which abuts against and slidingly seals against the shoulders 358 as shown in FIG. 3. In this manner, the air delivered to the mask frame can be redirected through the pillow assembly 100 and into the user's nares. The attachment sleeve 150 can be provided with an attachment portion 154 for receiving the pillow 110. The attachment portion 154 can be provided with a series of ribs or channels configured to interface with a plurality of annular ribs 114 and/or channels provided on an annular tube (or stem) forming an attachment portion of each pillow 110.

Figure 6A:
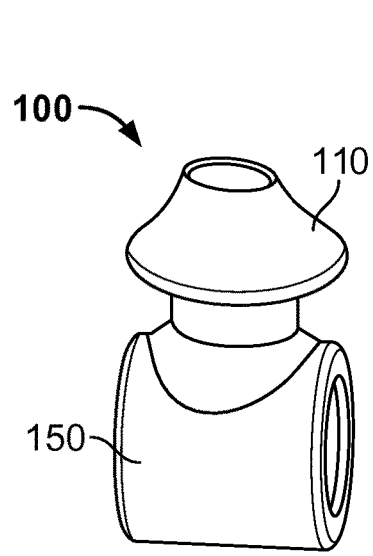
FIGS. 6A-E illustrate various exemplary nasal pillows and configurations for use with the ventilation and positive air pressure systems of FIGS. 1-2.
Figure 6B:
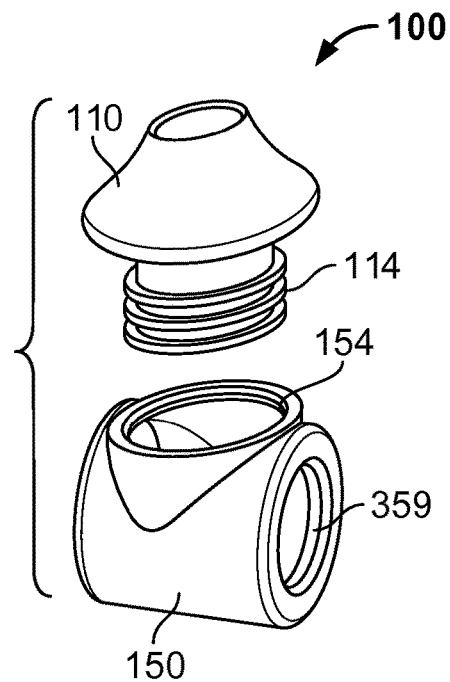
Figure 6C:
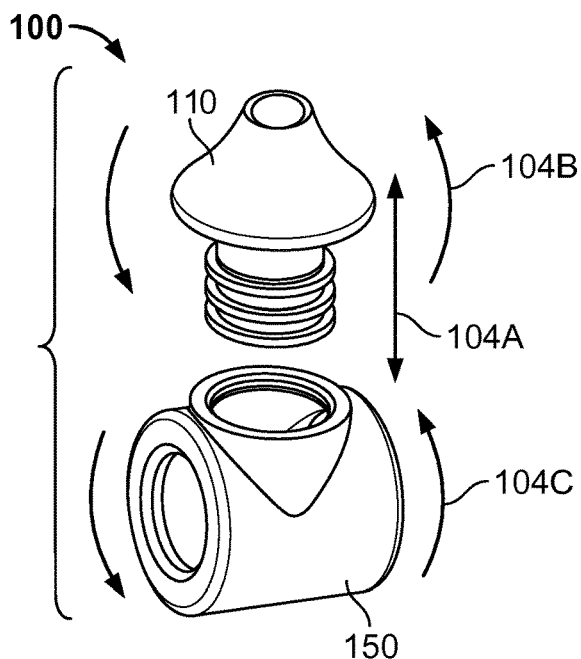
Figure 6D:
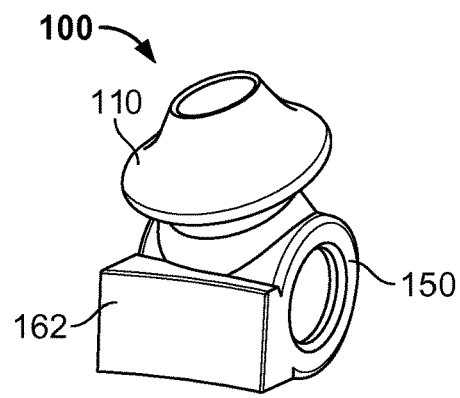

In particular FIG. 6D illustrates an air conform bladder 162 which can be formed as part of the attachment sleeve 150. The air conform bladder 162 can be formed of a malleable or flexible material, and have a hollow cavity defined thereby which receives pressurized gas from the interior of the attachment sleeve 150 when attached to the mask frame (not shown here). In this manner, as the pressure rises or is increased when the system is on, the air conform bladder becomes partially inflated and acts similar to a balloon. The air conform bladder 162 can then rest against the maxilla and provide an air cushioned interface between the mask and the user's face. In some embodiments, the air conform bladder is formed directly on the core frame, as part of the nasal pillows devoid of an attachment sleeve, or a part of the attachment sleeve itself that can form in part the nasal pillow assembly.

The meshing or integration of the annular ribs 114 with the channels or ribs 154 provided in the attachment sleeve allows for incremental adjustment of the relative height or radial positioning of the nasal pillow 110 with respect to the attachment sleeve 150, and thereby the mask frame or core, by changing which ribs are meshed with which respective channel. In this manner each nasal pillow can translate axially with respect to a pillow axis thus providing a first degree of freedom 104A. Additionally, the ribs and channels can slide with respect to one another when twisted about the pillow axis providing a second degree of freedom 104B which is rotational about a central axis of each pillow. Finally, the interior shoulder 359 can also slide with respect to its relative exterior shoulder of the mask frame 358 as shown in FIG. 3. so as to allow the sleeve, and the associated pillow to rotate about the axis of the right or left arm thus providing a third degree of freedom 104C. This sealing lip 359 allows for the attachment sleeve 150 to rotate about the mask along the mask frame axis thus providing a third degree of freedom 104C. Additional flexibility in the system can come from the nasal pillow itself. For example, the base portion of the nasal pillow, which functions like a trampoline or pivoting spring allows for the head or conical portion of the nasal portion to tilt or pivot about the stem or annular tube. This is made possible by varying the thickness or durometer of the base portion with respect to the head or conical portion and the stem or annular tube.

Figure 8:
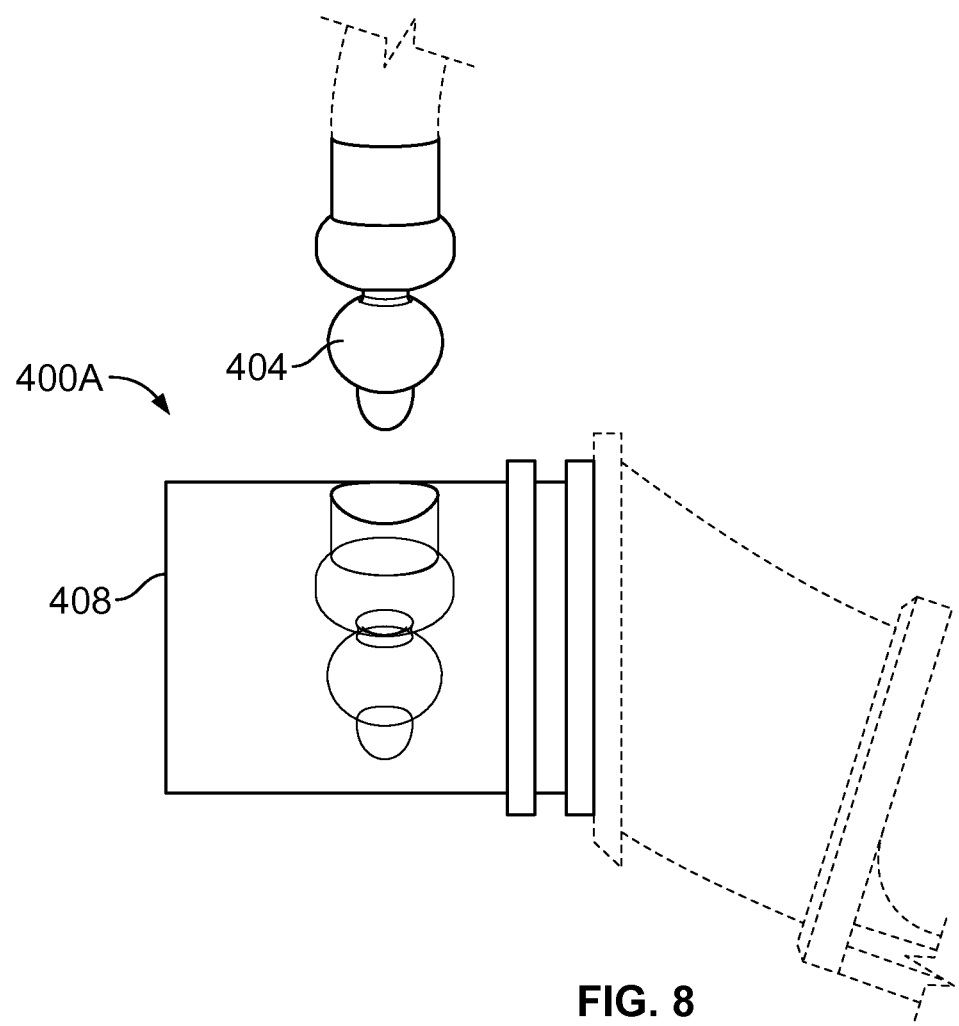
FIG. 8 illustrates an exemplary embodiment of a potential headgear connection interface for use with the ventilation and positive air pressure systems of FIGS. 1-2.
Figure 9:
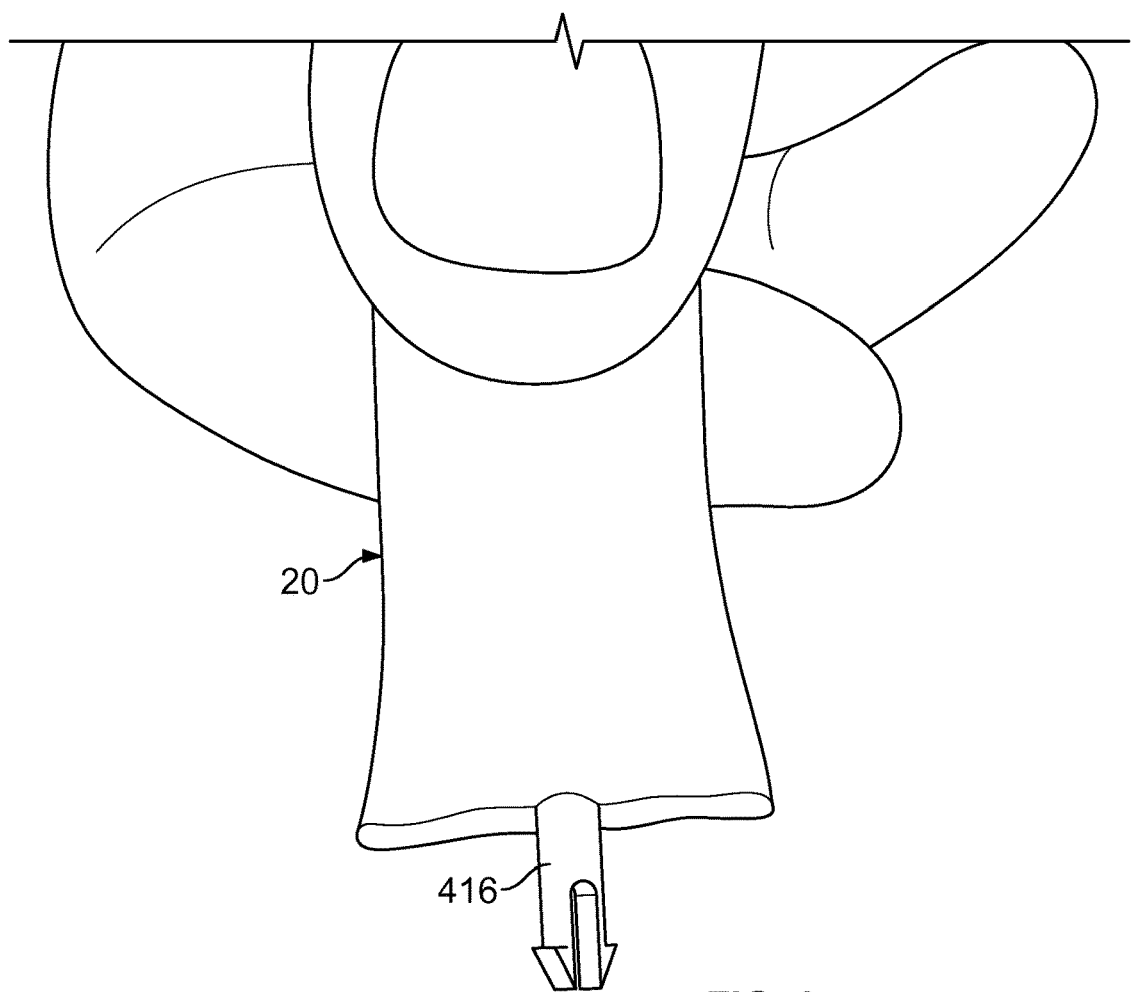
FIG. 9 illustrates another exemplary embodiment of a potential headgear connection interface for use with the ventilation and positive air pressure systems of FIGS. 1-2.
Figure 10:
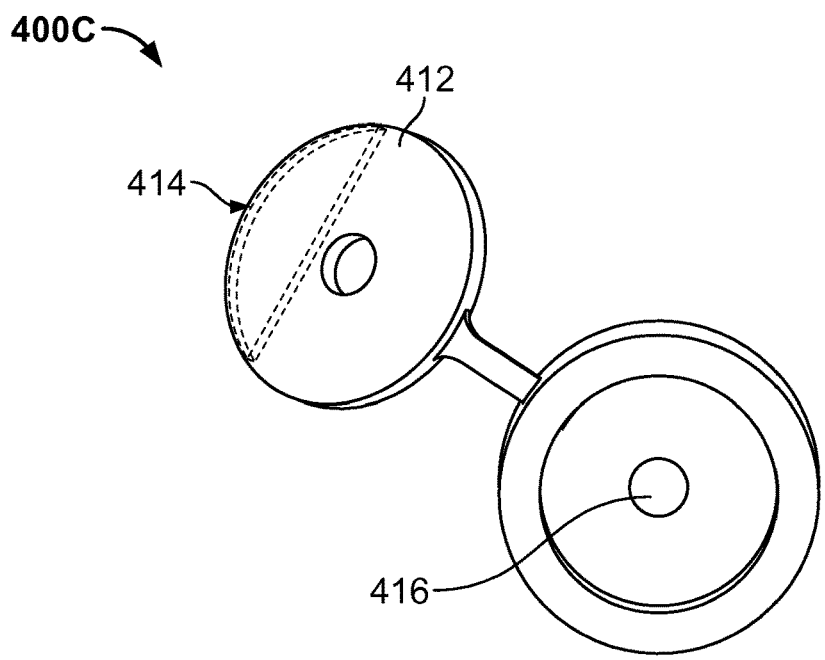
FIG. 10 illustrates a fitting for the potential headgear connection interface of FIG. 9.
Figure 11:
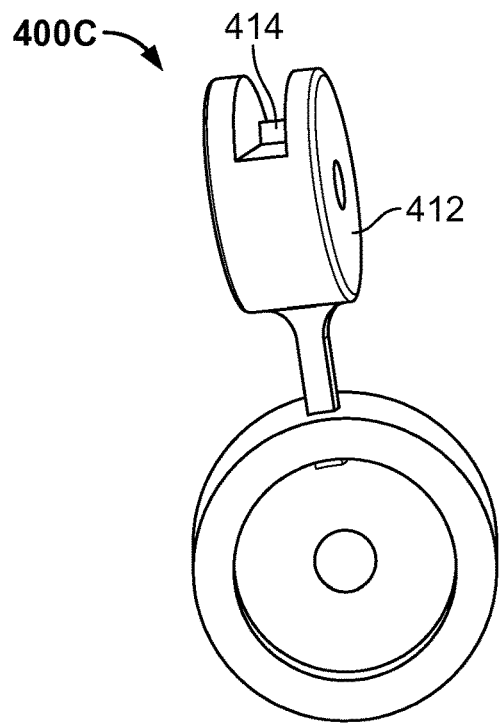
FIG. 11 illustrates another alternative fitting for the potential headgear connection interface of FIG. 9.
Figure 12:
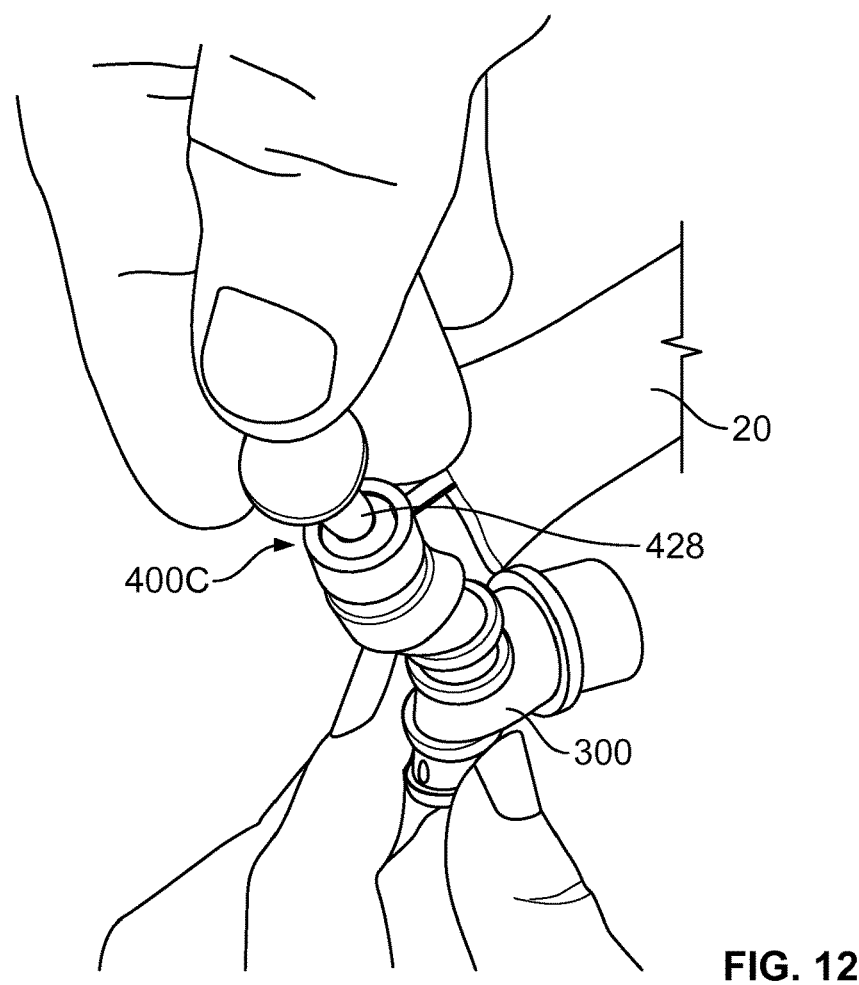
FIG. 12 illustrates a perspective view of an assembly procedure using the headgear connection interface of FIG. 9.

FIG. 8 illustrates another embodiment of the headgear connector 400A which utilizes a contoured barb 404 and a corresponding barb receiver 408. The barb can have a plurality of shapes including semi-spherical shapes as shown, or any other conceivable geometric shape with a correspondingly shaped receiver. In this embodiment the receiver is configured to be deformable or resilient so as to expand to initially accept the barb 404 when press therein. After the barb 404 is pressed into the receiver, an interference fit is formed and the barb will resist, to a certain degree, being pulled from the receiver 408.

FIGS. 9-12 illustrate yet another embodiment of a headgear connector 400C which utilizes a connector 412 which has two ends, one for attaching to the distal end of the mask frame or core 300, and the other for interfacing with the headgear 20. The headgear interfacing end is provided with an aperture 414 configured to receive a clip barb 416. The core end of the connector 412 has another corresponding aperture 416 through which a plug 428 can be provided so as to affix the connector 412 to the core 300. The two ends of the connector can be configured to rotate with respect to one another, as illustrated between FIGS. 10 and 11, so as to provide additional comfort to the user and allow the strap of the headgear to rest naturally with respect to the distal ends of the mask frame.

Figure 14:
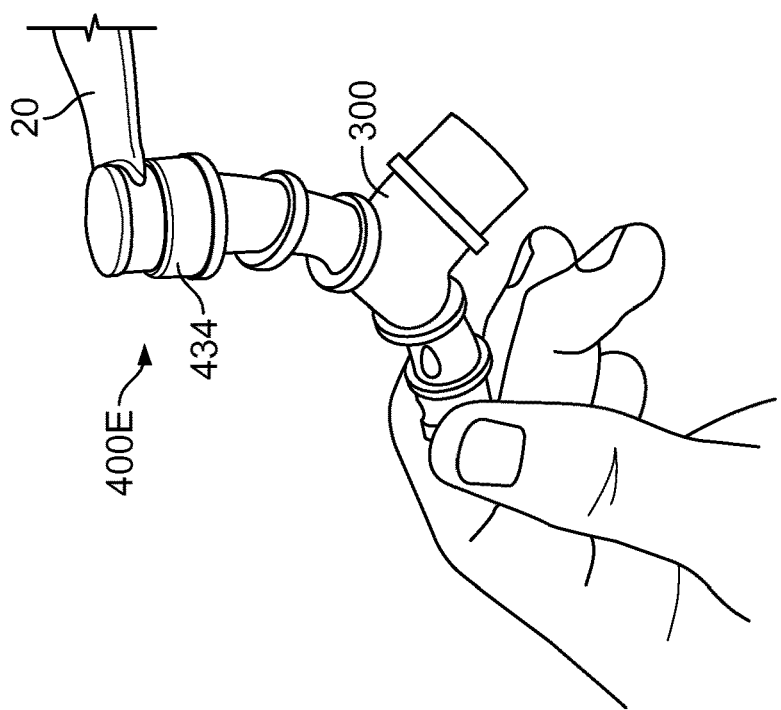
FIG. 14 illustrates an alternative perspective view of the assembly procedure of the embodiment of FIG. 13.
Figure 13:
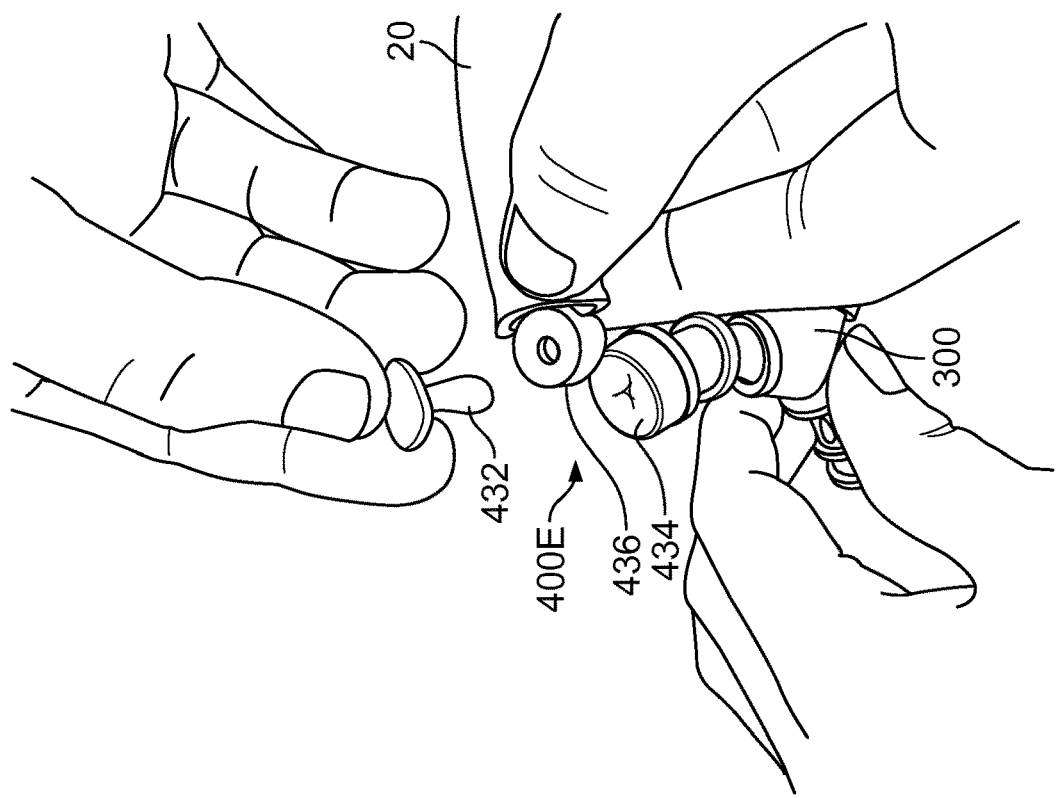
FIG. 13 illustrates a perspective view of an assembly procedure of yet another exemplary embodiment of a potential headgear connection interface for use with the ventilation and positive air pressure systems of FIGS. 1-2.
Figure 15:
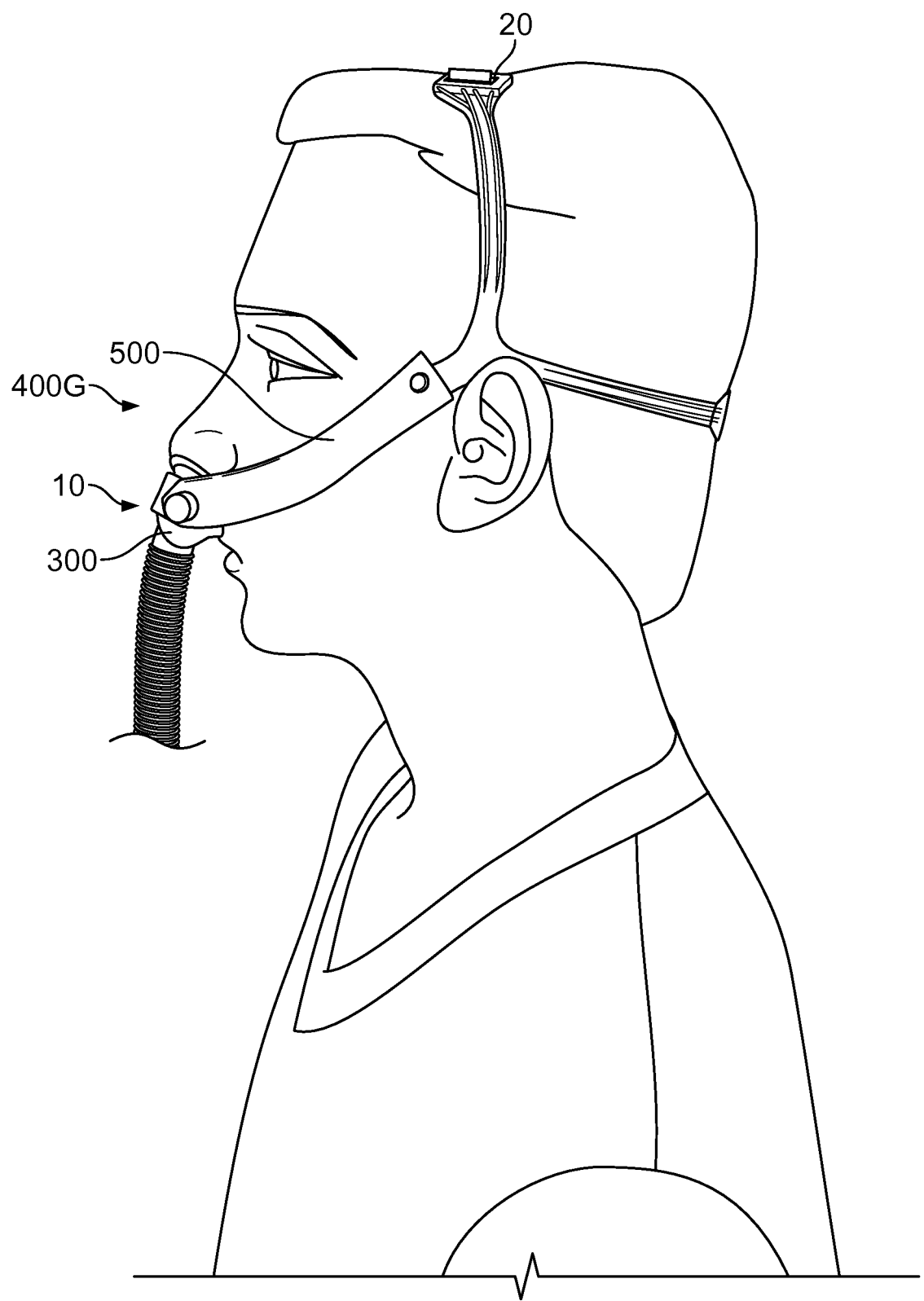
FIG. 15 illustrates a perspective view of a user wearing yet another exemplary embodiment of a potential headgear connection interface for use with the ventilation and positive air pressure systems of FIGS. 1-2.
Figure 16:
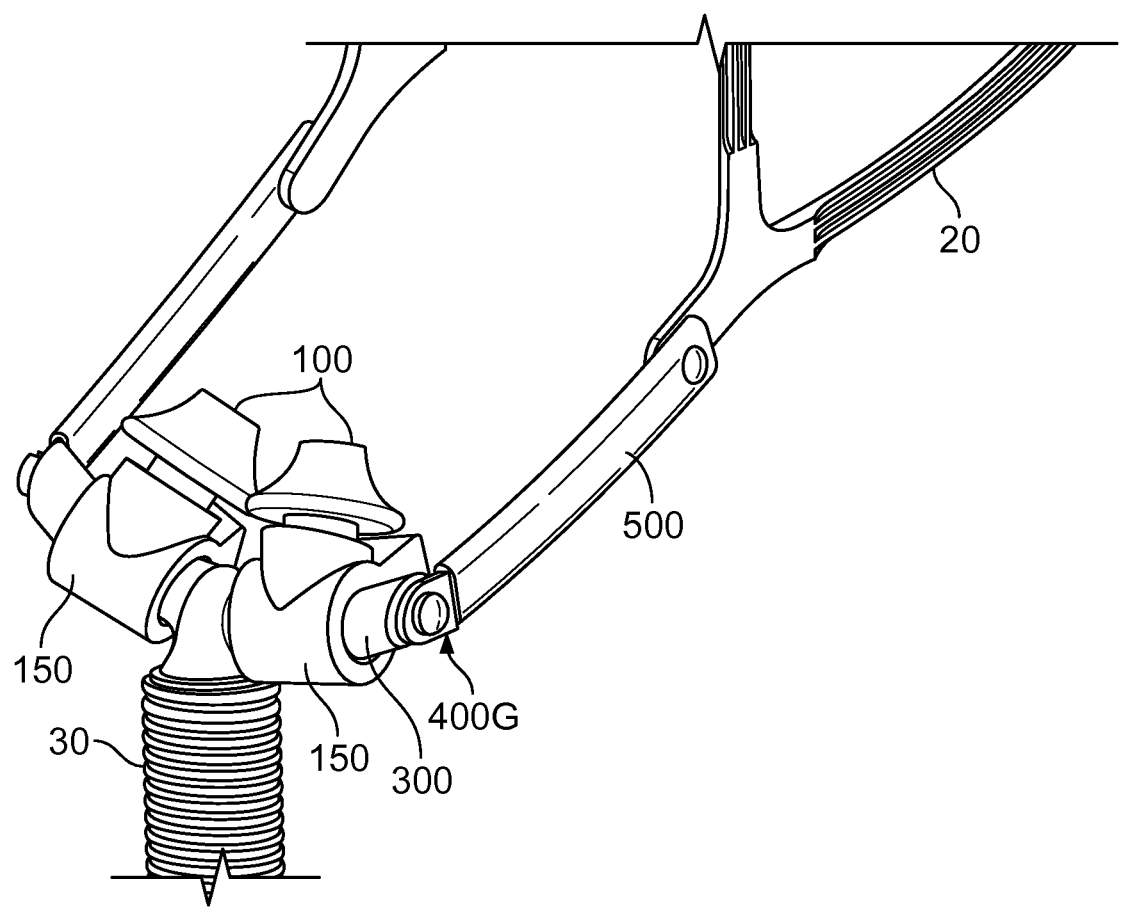
FIG. 16 illustrates a perspective view of the assembled exemplary embodiment of a potential headgear connection interface of FIG. 15.
Figure 17:
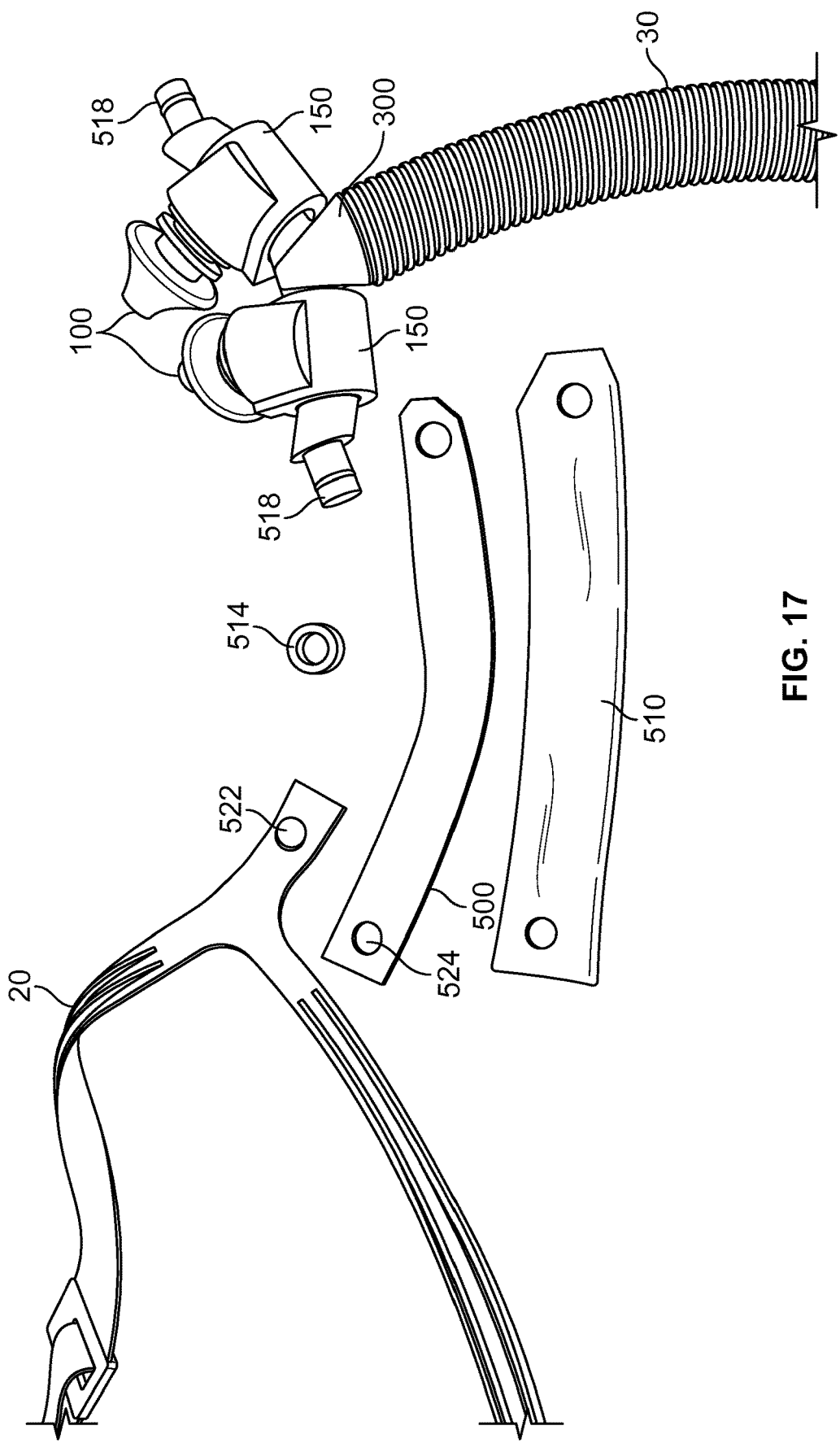
FIG. 17 illustrates a perspective exploded view of the exemplary embodiment of a potential headgear connection interface of FIG. 15.
Figure 18:
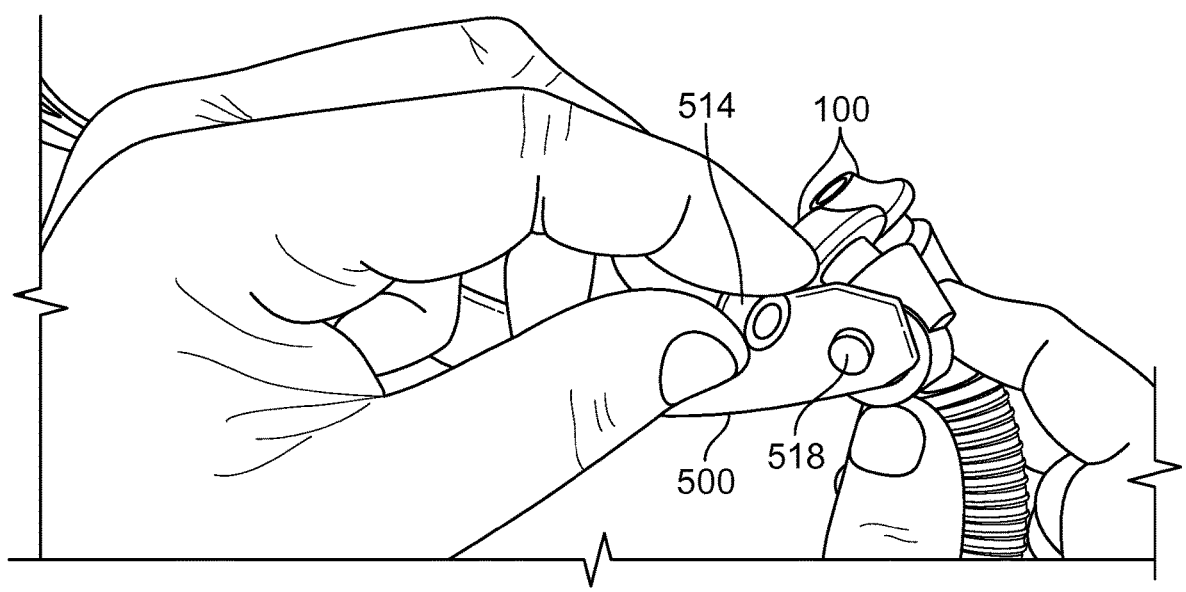
FIG. 18 illustrates a perspective view of an assembly procedure of the exemplary embodiment of a potential headgear connection interface of FIG. 15.
Figure 19:
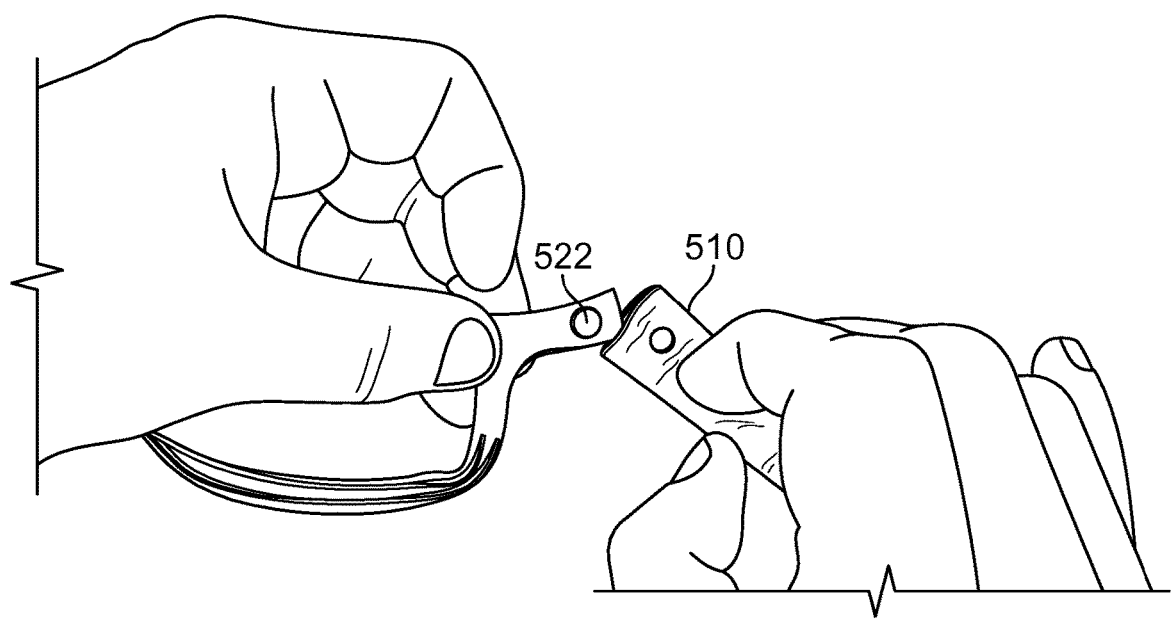
FIG. 19 illustrates a perspective view of another portion of the assembly procedure of the exemplary embodiment of a potential headgear connection interface of FIG. 15.

FIGS. 13-14 illustrate yet another embodiment of a headgear connection interface 400E in which a strap of the headgear 20 is provided with a simple annular washer end 436. A plug 432 can then be provided the annular washer end 436 and have an interference fit with a corresponding plug adapter end 434 provided about the distal ends of the mask frame 300.

FIGS. 15-19 illustrate various views of yet another embodiment of a headgear connection interface 400G in which a strap of the headgear 20 is provided with a deformable side piece 500 provided between the headgear 20 and the mask frame 300. The deformable sidepiece 500 can attach to each arm using an interference interconnector comprising a male connection 518 and a female connector 514 as well as attached to the headgear 20 by means of a male connector 522 and female aperture 524. It will be appreciated that the relative male of female connectors or apertures can be located selectively about either the deformable sidepiece or the interference interconnector. As shown, the deformable sidepiece 500 can be configured to attach to the each respective arm at various angular positions, or in other words rotate with respect to the mask frame 300. Additionally, the deformable sidepiece 500 can be provided initially as a planar member, which can then be selectively deformed out of plane so as to conform about the facial contours of a user. In this manner the deformable side piece can be shaped so as to follow the contours of the user's cheeks without touching them, or alternatively touch the cheeks but equally distribute any pressure applied thereto.

It should be understood that of the various connectors described herein, some versions are configured to have the headgear connect to the mask frame in a fixed connection (non-rotating), some allow for free rotation connection (no interference or stops), and some have interference mechanisms to selectively rotate or be positioned angularly about the mask frame.

In one instance the deformable sidepiece is formed of a shape retaining plastic. This plastic can have a general deformation characteristic along a single plane while maintaining some rigidity in a second plane. Other types of deformable plastic can be deformed along multiple planes. In one embodiment the cross-section of the deformable sidepiece is rectangular. The curvature of the deformable sidepiece along a particular plane (see FIGS. 15 and 17) can be preset or formed to transfer the force of the head gear system around certain features of the user's face. Since user's faces have three-dimensional features the deformable sidepiece can then conform to the remaining features of the user's face. Thus, allowing a customizable headgear system that maintains a balance between rigidity and flexibility, while being conformable to a user's unique facial features.

It will be further appreciated that the deformable sidepiece 500 might cause a certain degree of discomfort to a user. As such, a malleable sleeve 510 can be provided which encompasses the deformable sidepiece 500. The malleable sleeve can be formed of fabric, silicone, or other comfort increasing material having any number of desired attributes, such as heat transfer rate, elasticity, softness, etc.

Figure 20:
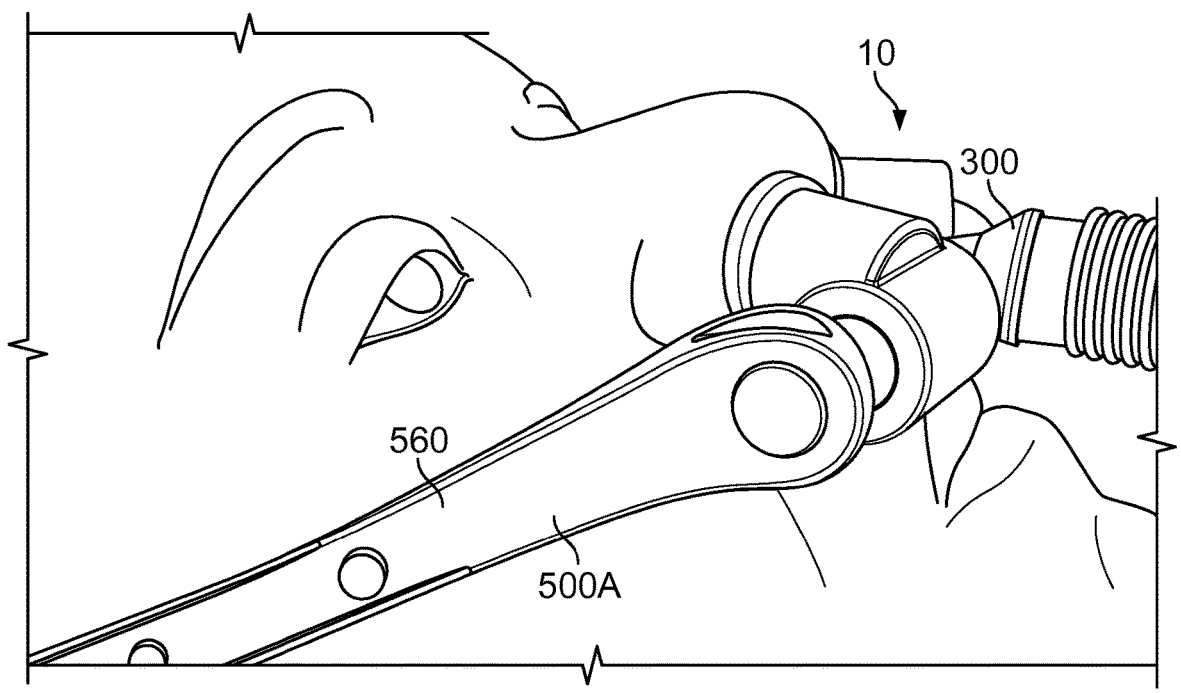
FIG. 20 illustrates a perspective view of a user wearing yet another exemplary embodiment of a potential headgear connection interface for use with the ventilation and positive air pressure systems of FIGS. 1-2.

FIG. 20 illustrates a deformable sidepiece 500A which has a silicone shell 560 having a malleable shape retaining core.

Figure 21:
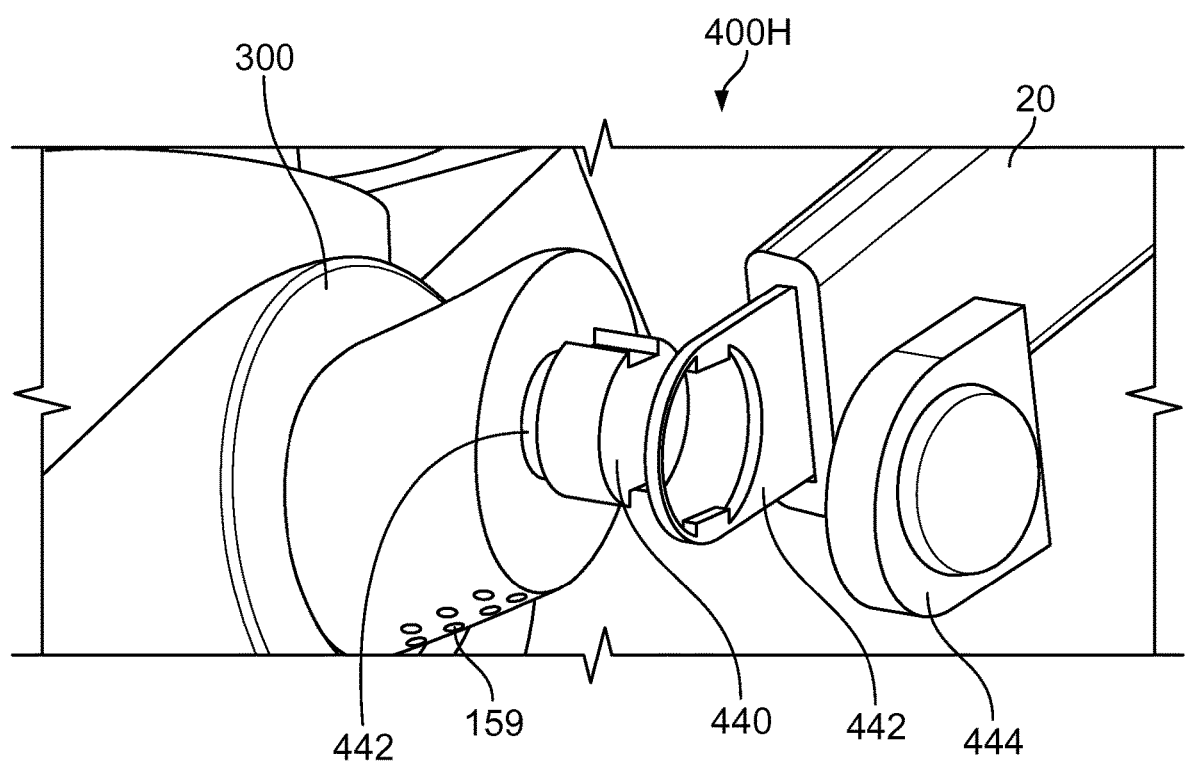
FIG. 21 illustrates a perspective exploded view of a yet another exemplary embodiment of a potential headgear connection interface for use with the ventilation and positive air pressure systems of FIGS. 1-2.

FIG. 21 illustrates yet another headgear connection interface 400H which includes a keyed post 440 located about a distal end of the mask frame 300 and keyed opening 442 which slid through the keys to an inner portion 442 with a smaller diameter which allows free rotation. The assembly can only be separated when angularly positioned correctly so as to align the keys. It will be appreciated that the keys should be provided out of phase from each other in normal angular positions between the mask frame 300 and the headgear 20 while being worn. In order to ensure that the keyed components do not separate unintentionally, a cap 444 can be provided which prevents unintentional separation.

Figure 22:
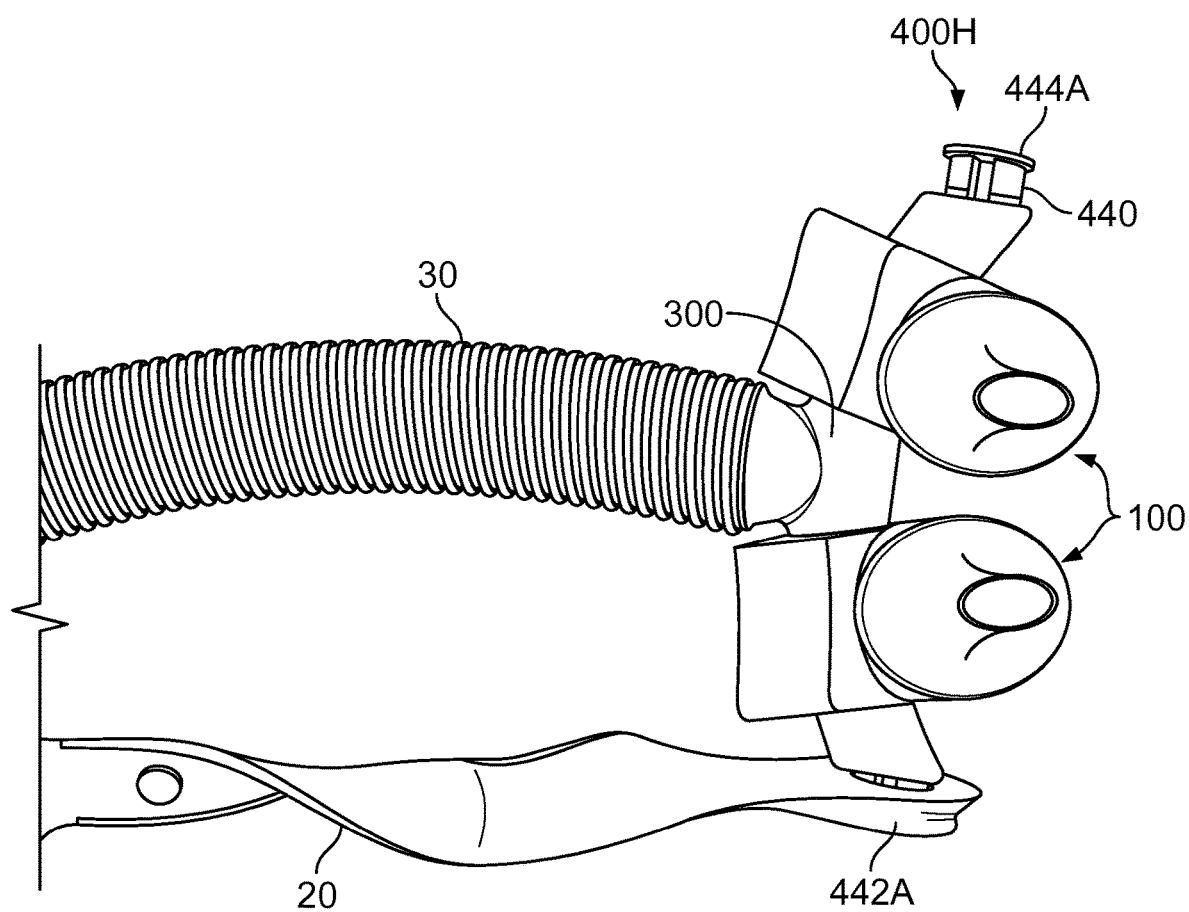
FIG. 22 illustrates a perspective view of yet another partially assembled exemplary embodiment of a potential headgear connection interface for use with the ventilation and positive air pressure systems of FIGS. 1-2.

FIG. 22 illustrates another keyed embodiment, similar to that of FIG. 21. having an alternative strap portion 442A, which covers the hardware, i.e. the keyed post 440 and the associated connector inside the strap 442A, so as to improve comfort and reduce the likelihood of catching the mask on something while shifting during sleep and thus tearing the mask off the user's face. This embodiment utilizes a similar plug 444A to cover the connection from the outside of the strap 442A and thus prevent premature decoupling or catching.

Figure 23A:
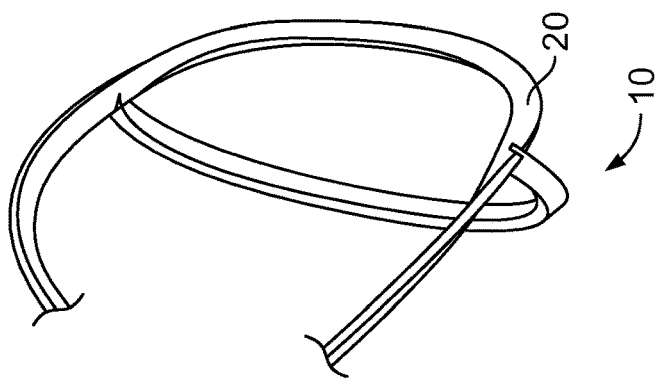
FIGS. 23A-C illustrate exploded side and front views, respectively, of an alternative core or mask frame assembly for use with the ventilation and positive air pressure systems of FIGS. 1-2.
Figure 23A:
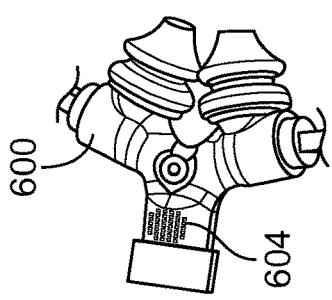
Figure 23C:
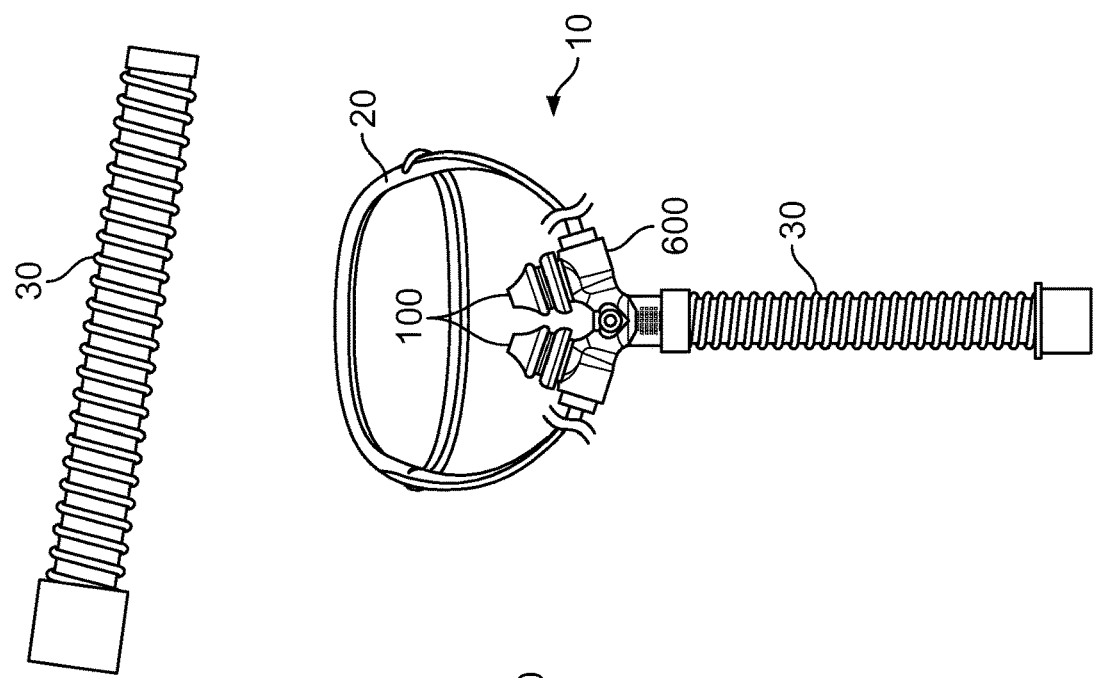
Figure 23B:
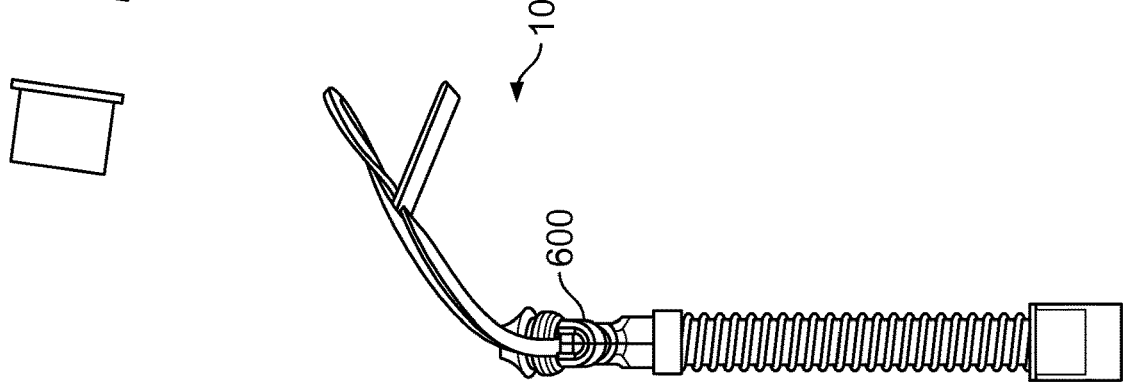

FIGS. 23A-C illustrate an alternative embodiment of a mask frame 600. This mask frame is more rigid and instead of interfacing with the nasal pillow assembly 100 using a rotatable sleeve, the arms of mask frame 600 are rigid and do not provide rotation of the pillow assemblies 100 about the respective arm portions. This embodiment provides increased stability for headgear attachment and facial placement purposes. In this embodiment the nasal pillows are still permitted to rotate about the pillow's central axis, wherein the pillows can have an elliptical cross section.

In this embodiment a plurality of washout vents 604 can be provided in a central portion of the mask frame 600. Additionally, the headgear 20 can be attached to the mask frame 600 using any of the previously discussed headgear attachment interfaces.

Figure 6E:
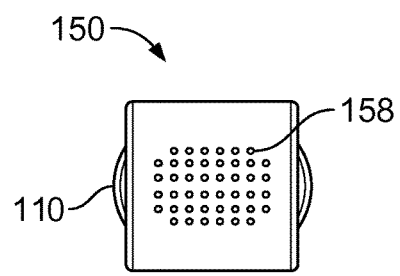

FIGS. 6E, 21 and 23A all show various placements of $CO_2$ washout vents. Being at a bottom portion of the pillow assembly 100, on the attachment sleeve 150 as shown by 158 in FIG. 6E, at the ends of the right or left arms, as shown by 159 in FIG. 21, and on the mask frame at a central portion as shown by 604 in FIG. 23A. It will be appreciated that any one of these placements either alone or in any combination is within the scope of the present invention. The $CO_2$ washout vents may be comprised of a material that has silicone knife coated across it. In other embodiments the $CO_2$ vent is a plurality of holes that have been formed therein.

It is contemplated that the wall thickness and/or durometer of the nasal pillow portion can be varied. In one exemplary embodiment the flat underside portion which connects the bell like top of the nasal pillow to the tube portion may have either a thinner wall portion then the flared bell like portion and tube portion or may have a lower durometer value. This thinner wall or lower durometer value allows the tube connected to the flat underside to collapse into the bell like portion when pressure is exerted on the bell like portion. When the nasal pillows are formed of the silica material or silken like material the nasal pillow returns to its original state when no pressures being exerted on it. Again this allows for the flared bell like portion to pay that about the tube portion when being inserted into the nasal region. The collapse ability again helps reduce pressure exerted onto the nasal region while at the same time helping to find an optimal position that forms a good seal between the nasal pillow and each of the nostrils.

It will be appreciated that in certain embodiments the headgear can cause a direct tightening of the pillows into the nostrils of the user, thus having a direct correlation to a sealing force. In yet other embodiments, for example, when providing an air conform bladder, as discussed with reference to FIG. 7, the force applied by the headgear can be partially directed through the air conform bladder and into the maxilla to provide a primarily a positioning force, where the sealing force can be adjusted by changing the relative placement of the mask frame on the face, which is held by the positioning force. In yet additional embodiments, the nasal pillows can be caused to enter into, and hold their relative position by the elastic properties of the pillows being exerted onto the inner walls of the user's nostrils or nares without the use of headgear altogether.

Figure 24:
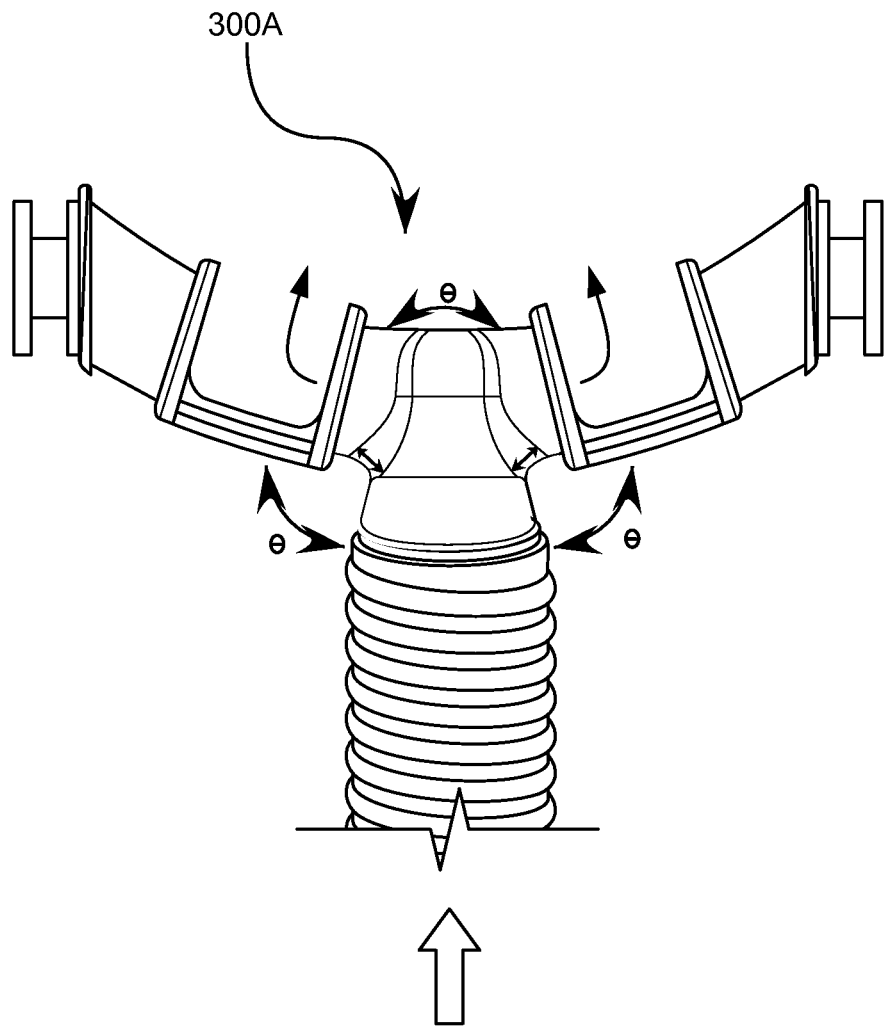
FIG. 24 illustrates an alternative embodiment of a mask frame having adjustable arm portions.

FIG. 24 illustrates another alternative core or mask frame 300A where the right and left arms are arranged to pivot or rotate about the center of the core. In some versions the right and left arms can form a 180 degree angle between each other, making the core look more like "T" shape, each arm can then be repositioned to form a "Y" shape. The angles between each arm can range from several degrees to greater than 180 degrees. However, most users will have the arms angled somewhere less than 180 degrees. This additional degree of freedom presented by this alternative core 300A can also work with the attachment sleeves, rotatable nasal pillows as described above for a customizable fit.

In some versions the rotation of the arms is a constant and consistent motion, which can be enabled by a pressure sliding fit between the pivoting arm and the core. In other versions discrete angled positions are enabled by each arm locking into a groove or channel or other distinct locking mechanism. Some of the rotation mechanisms can function similar to the locking and rotation features of the headgear interface assembly.

FIGS. 25-28 illustrate yet another alternative embodiment of a mask frame 300B-D. In these embodiments the mask frame 300B-D can have one of more apertures 710 and 710A respectively, the apertures being provided about distal ends of the right and left arms of the mask frame 300B-D so as to provide fluid communication between the air supply channel within the mask frame 300B-D and a pair of air cushion straps 750 provided about the distal ends of their respective right and left arms. The air cushion straps 750 can have an annular wall which forms a cavity 740 therein, each air cushion strap 750 having an aperture 754 which provides an interface through which the apertures 710 or 710A can provide fluid communication from the air channel of the mask frame 300B-D into the cavity 740. The mask frame 300B-D can have a sealing lip 714 which interfaces with an edge of the aperture 754 to create a seal between the air cushion straps 750 and the mask frame 300B-D such that positive air pressure provided to an interior portion of the mask frame is communicated into the cavity 740 causing the air cushion strap to expand and provide a cushioning effect increasing the comfort of the strap which may rest against the user's face in certain configuration.

In some embodiments the air cushion straps can be provided with a plurality of $CO_2$ washout vents 768 along an exterior wall, such that $CO_2$ can be vented out of the system through the air cushion straps. These $CO_2$ washout vents 768 can be provided by knife coating or otherwise applying a silicone layer over a flexible and permeable material, which then allows for the escape of $CO_2$ but do not cause a significant drop in pressure of the system such that the required therapeutic pressure is lost or that the air cushion straps do not inflate.

Figure 25:
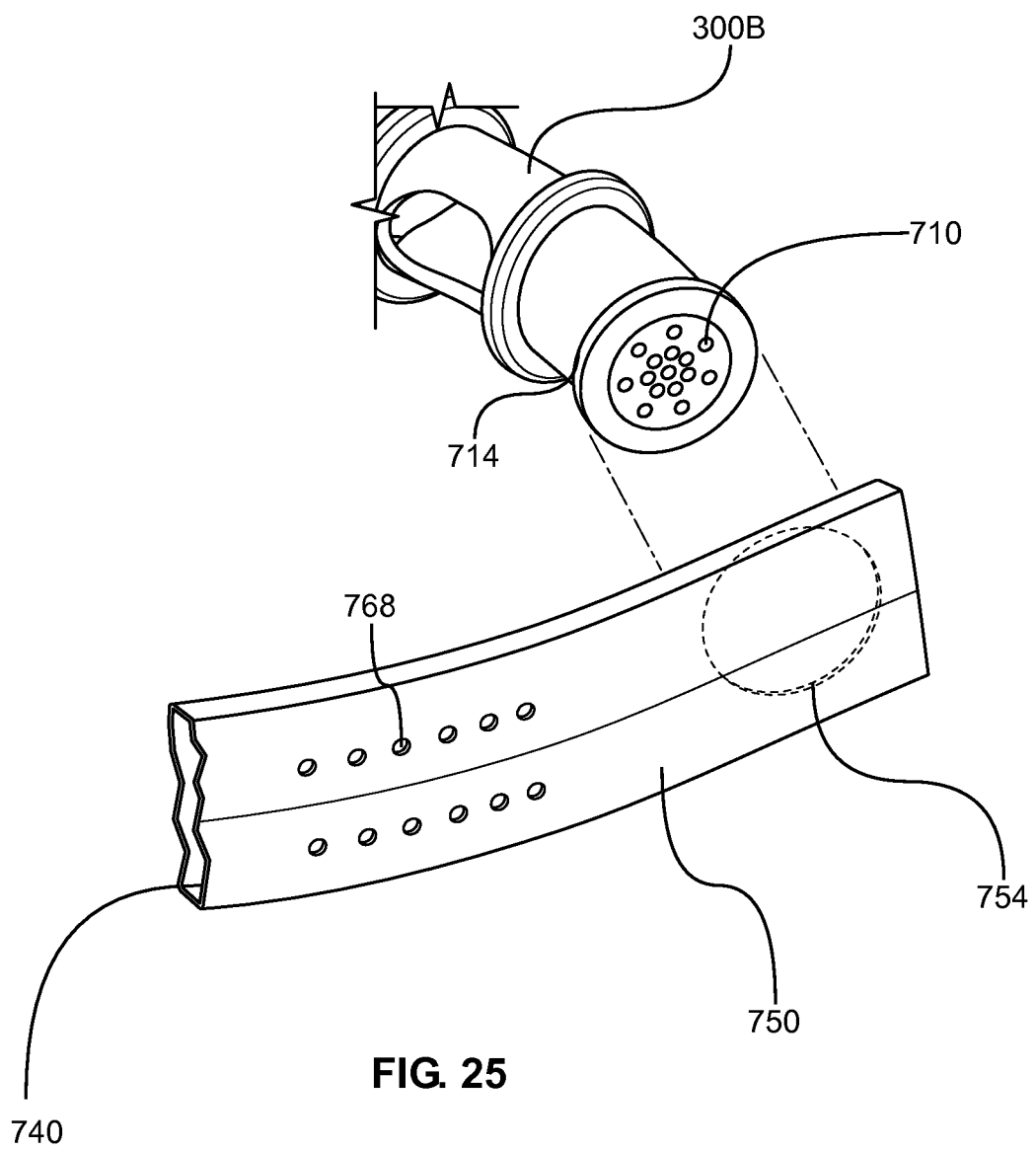
FIG. 25 illustrates a perspective end view of a frame and a partial view of an inflatable strap assembly in accordance with yet another embodiment of a headgear connection interface.
Figure 26:
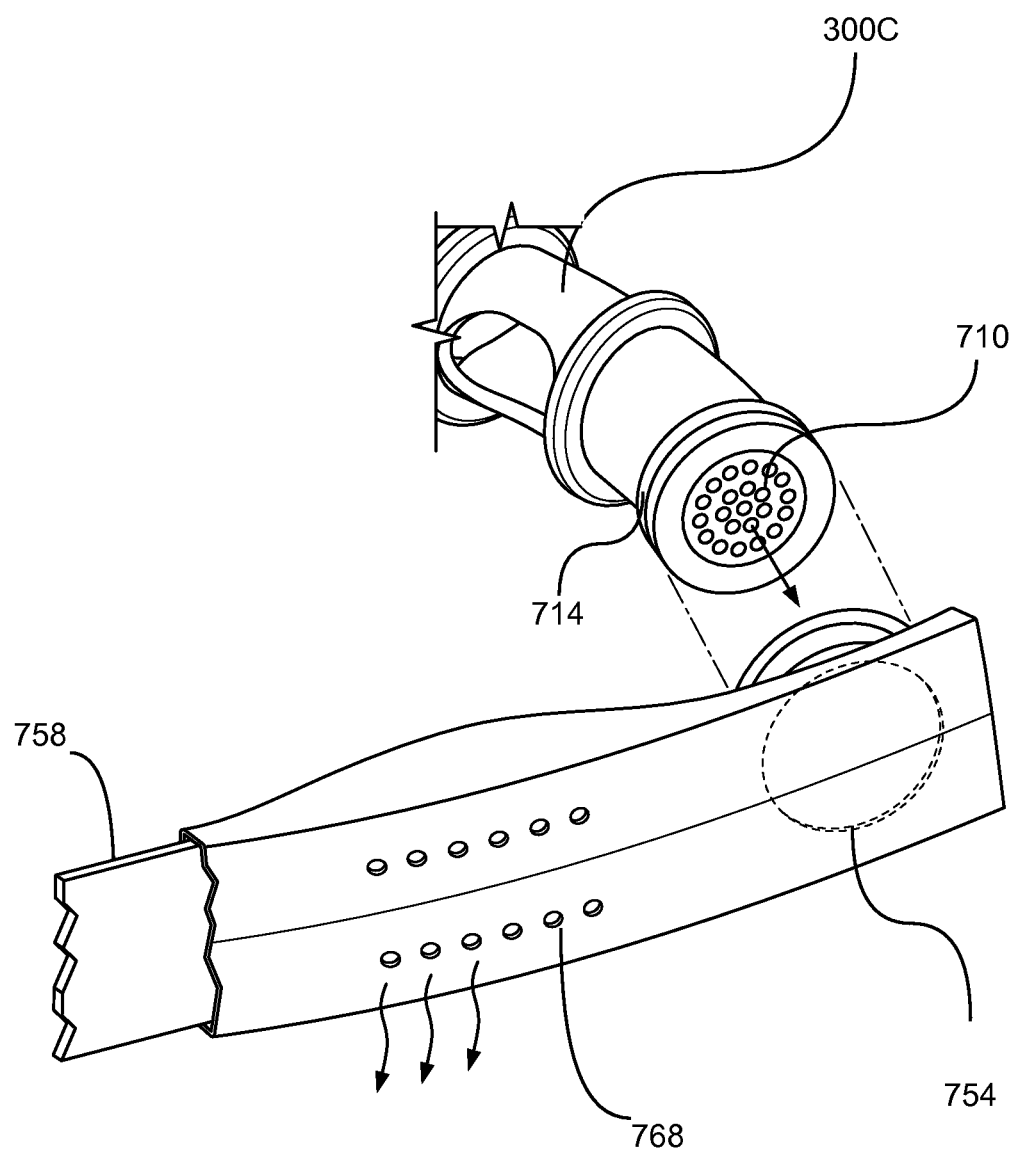
FIG. 26 illustrates a perspective end view of a frame and a partial view of an inflatable strap assembly having a deformable core in accordance with yet another embodiment of a headgear connection interface.

It will be appreciated, and as particularly as shown between FIGS. 25 and 26 that the air cushion straps 750 can be provided as completely hollow and as a unitary material as shown in FIG. 25, or alternatively as shown in FIG. 26, having a deformable shape retaining core 758, being similar in construction to the deformable sidepiece as discussed above. The deformable shape retaining core can be provided in a core portion or otherwise provided within the air cushion cavity, or within its own cavity, such that deforming the deformable shape retaining core can provide the entire air cushion strap with a certain desired contour or shape. It will be understood that in preferred embodiments the deformable shape retaining core can be provided along an exterior inner wall such that the air cushion straps inflate in a direction toward the user's face thus creating an air cushion there between. It will thus be further understood that holes can be selectively provided through the deformable shape retaining core such that they communicate with the $CO_2$ vents provided therethrough.

Figure 27:
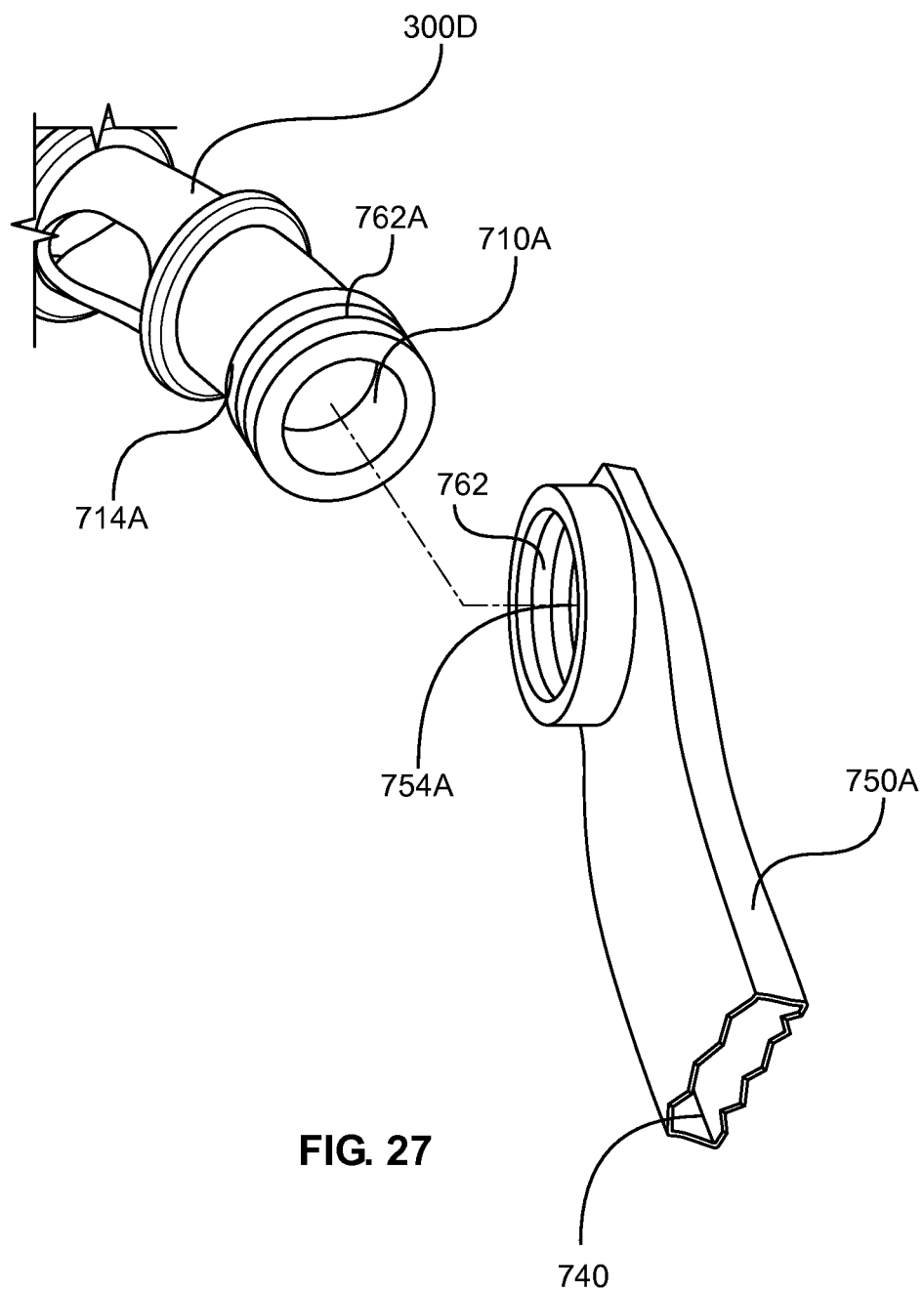
FIG. 27 illustrates a perspective end view of a frame and a partial view of an inflatable strap assembly having a deformable core in accordance with yet another embodiment of a headgear connection interface.
Figure 28A:
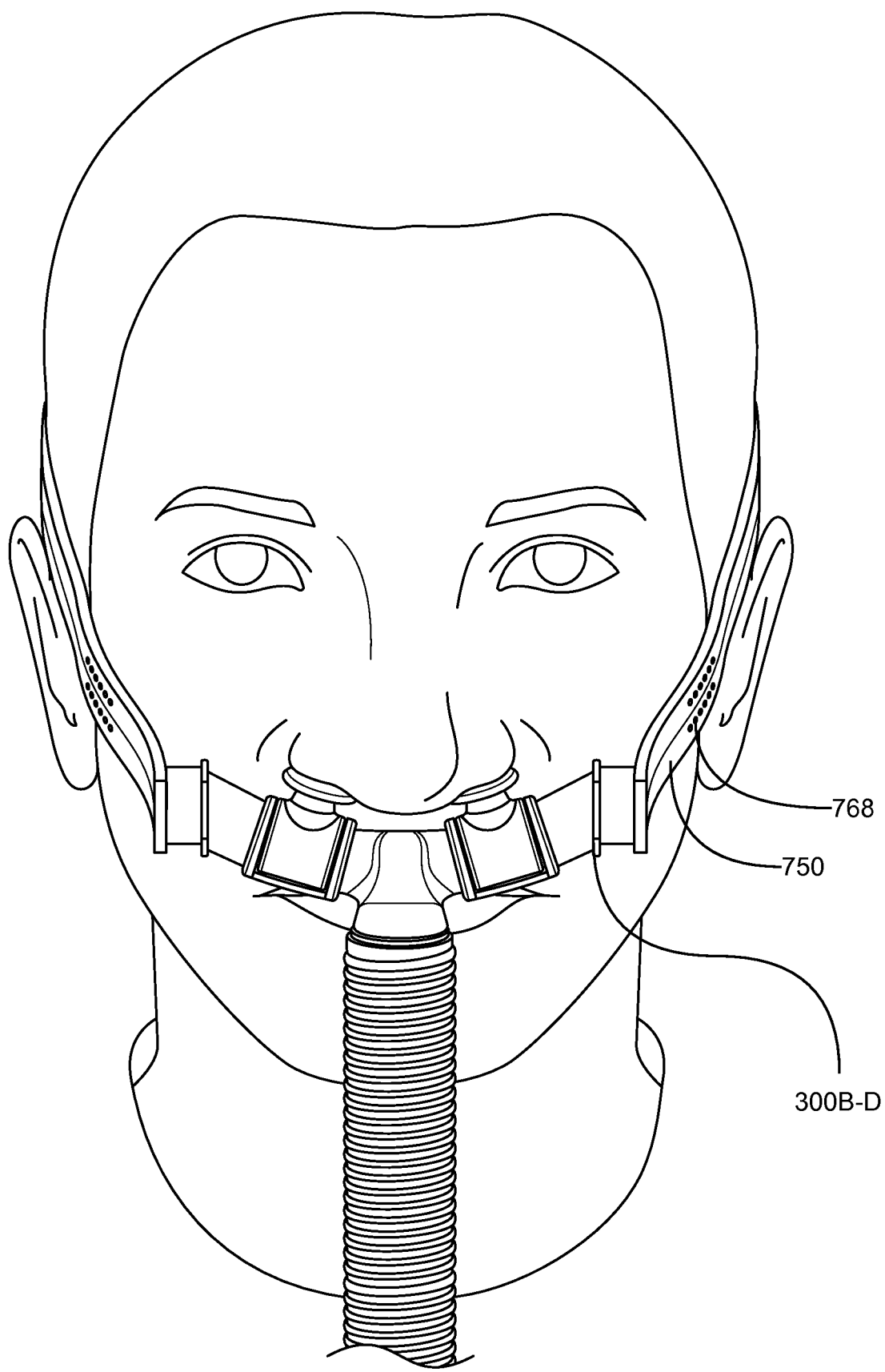
FIGS. 28A-B illustrate a front view of a user wearing any one of the embodiments as shown in FIGS. 25-27 illustrating an uninflated and inflated configuration of an inflatable side strap.
Figure 28B:
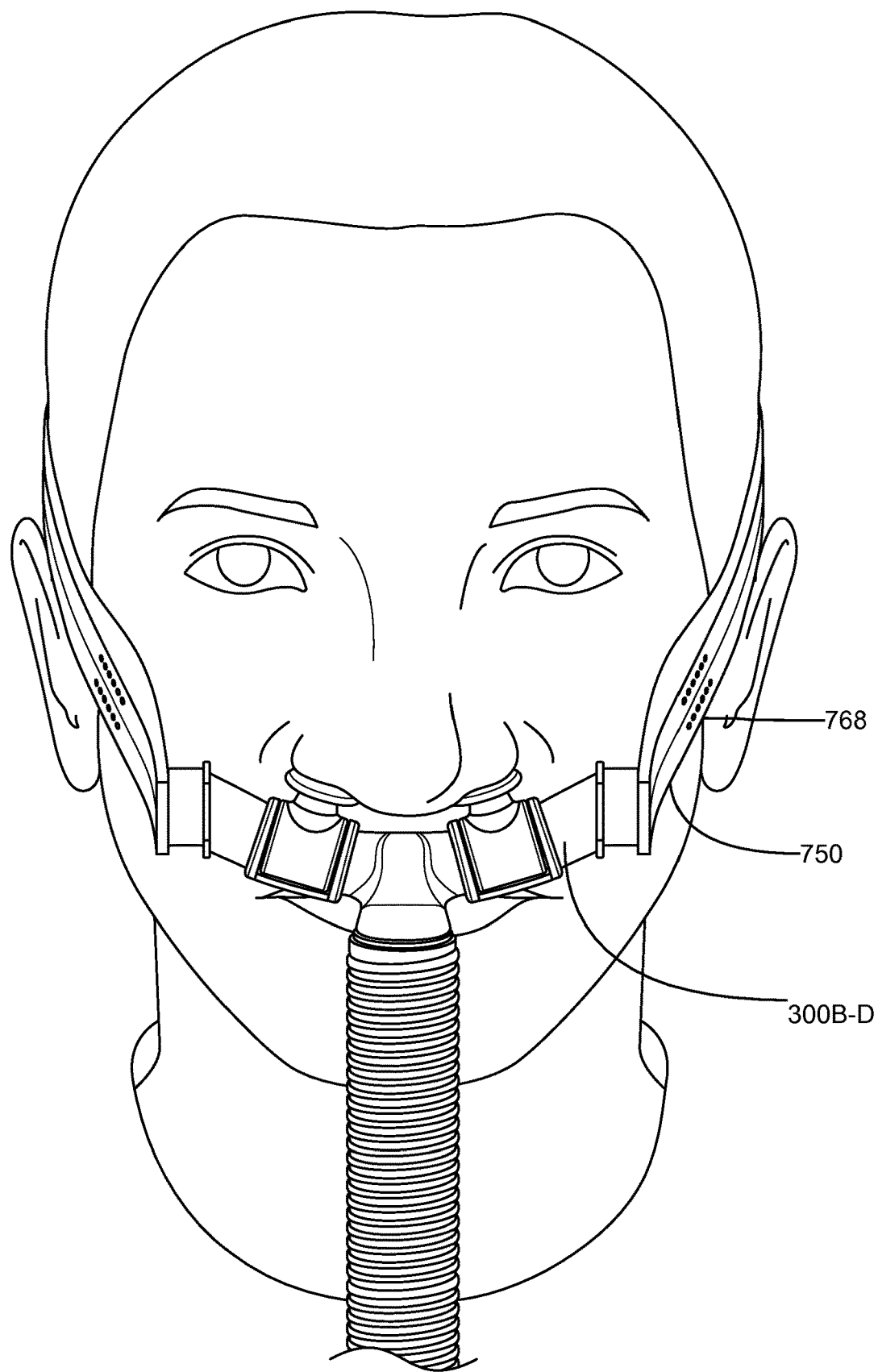

FIG. 27 illustrate yet another embodiment alternative embodiment of a mask frame 300D being similar to the embodiment of FIGS. 25-26. In this embodiment the mask frame 300D can also have one of more apertures 710A, the apertures being provided about distal ends of the right and left arms of the mask frame 300D so as to provide fluid communication between the air supply channel within the mask frame 300D and a pair of air cushion straps 750A provided about the distal ends of their respective right and left arms. The air cushion straps 750A can have an annular wall which forms a cavity therein, each air cushion strap 750A having an aperture 754A which provides an interface through which the apertures 710A can provide fluid communication from the air channel of the mask frame 300D into the interior cavity of each strap. The mask frame 300D can have a deeper sealing lip 714A which interfaces with an edge of the aperture 754A or a female receiving portion as shown, the female receiving portion having an additional seal 762, which can be rubber or some other malleable material, which is provided therein so as to create a seal between the air cushion straps 750A and the mask frame 300D. In some embodiments a corresponding seal 762A can be provided about the sealing lip 714A so as to increase the seals effectiveness. In this manner positive air pressure provided to an interior portion of the mask frame 300D is communicated into the cavity 740, thus causing the air cushion strap 750A to expand or otherwise inflate and provide a cushioning effect. This inflated cushion increases the comfort of the strap which may then conform to and rest against the user's face in certain configuration and equally distribute any pressure. The air cushion strap 750A can similarly be provided with a plurality of optional $CO_2$ washout vents provided therein, which can be formed from applying silicone over the flexible material forming the cushion strap and allows the $CO_2$. In some instances the silicon is applied using a knife-coating method.

FIGS. 6E, 21, 23A, and 25A all show various placements of $CO_2$ washout vents. Being at a bottom portion of the pillow assembly 100, on the attachment sleeve 150 as shown by 158 in FIG. 6E, at the ends of the right or left arms, as shown by 159 in FIG. 21, on the mask frame at a central portion as shown by 604 in FIG. 23A, or on the side straps as shown by 768 in FIG. 25A. It will be appreciated that any one of these placements either alone or in any combination is within the scope of the present invention. The $CO_2$ washout vents may be comprised of a material that has silicone knife coated across it. In other embodiments the $CO_2$ vent is a plurality of holes that have been formed therein.

In some alternative embodiments the $CO_2$ washout vents can be formed on the sidepiece of the headgear system where the sidepiece does not inflate. In one version a flexible tube runs along the sidepiece that has CO2 washout vents formed therein, but does not expand (or negligibly expands) with the positive air pressure being supplied to the system. Silicone and other rubber like materials tend to be more soluble to CO2 and repel oxygen and other gas molecules.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Further, discussion with regard to any of the specific features is intended to be for illustrative purposes, with the understanding that any feature discussed herein can be used in combination with any number of other features in any combination from any of the various embodiments. Accordingly, it is not intended that the invention be limited, except as by the claims set forth below.

We claim:

1. A mask and headgear assembly comprising:
   a mask frame, the mask frame comprising:
      a core having an inlet connector configured for receiving a supply of pressurized gas from a delivery tube;
      a right arm extending from the core;
      a left arm extending from the core, wherein each of the right and left arms forms an air pathway through each respective arm, wherein each arm includes a first aperture for supplying the supply of pressurized gas to a patient's airways; and
   a headgear interface located about a distal end of each arm, the headgear interface being configured to be attached to a headgear assembly, each headgear interface comprising a second aperture configured for communicating a portion of the supply of pressurized gas to an interior portion of the headgear assembly.

2. The mask and headgear assembly of claim 1, wherein the headgear assembly includes an inflatable cushion configured to inflate in response to the supply of pressurized gas delivered through the second aperture of each arm.

3. The mask and headgear assembly of claim 2, wherein the inflatable cushion includes a deformable core configured to be selectively deformed and retain a deformed shape.

4. The mask and headgear assembly of claim 2, wherein the inflatable cushion is configured to attach to each respective arm at various angular positions.

5. The mask and headgear assembly of claim 2, wherein the inflatable cushion is initially planar in an uninflated state.

6. The mask and headgear assembly of claim 5, wherein the inflatable cushion is configured to be selectively deformed out of plane so as to conform about a user's facial contours.

7. The mask and headgear assembly of claim 2, wherein the inflatable cushion includes a plurality of $CO_2$ washout vents on an exterior wall.

8. The mask and headgear assembly of claim 7, wherein the plurality of $CO_2$ washout vents comprise apertures formed from a knife-coated silicone layer formed on a flexible material.

9. The mask and headgear assembly of claim 1, wherein the mask frame includes a sealing lip configured to abut against and seal against a corresponding aperture in the headgear assembly.

10. The mask and headgear assembly of claim 9, wherein the headgear assembly includes a female receiving portion having a secondary seal.

11. The mask and headgear assembly of claim 1, wherein the headgear assembly includes a female receiving portion having a seal.

12. The mask and headgear assembly of claim 1 comprising at least a nasal pillow being connected over one of the first apertures of the right arm and the left arm, each nasal pillow being configured to communicate the supply of pressurized gas.

13. The mask and headgear assembly of claim 1, wherein the right and left arms are angled with respect to each other.

14. The mask and headgear assembly of claim 1, wherein the right and left arms pivot about the core.

* * * * *